United States Patent
Dorsch et al.

(10) Patent No.: US 7,598,241 B2
(45) Date of Patent: Oct. 6, 2009

(54) CARBOXAMIDE DERIVATIVES AND THEIR USE AS FACTOR XA INHIBITORS

(75) Inventors: Dieter Dorsch, Ober-Ramstadt (DE); Bertram Cezanne, Mörfelden-Walldorf (DE); Werner Mederski, Zwingenberg (DE); Christos Tsaklakidis, Weinheim (DE); Johannes Gleitz, Darmstadt (DE); Christoph van Amsterdam, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 585 days.

(21) Appl. No.: 10/543,109

(22) PCT Filed: Jan. 8, 2004

(86) PCT No.: PCT/EP2004/000061

§ 371 (c)(1), (2), (4) Date: Jul. 22, 2005

(87) PCT Pub. No.: WO2004/065369

PCT Pub. Date: Aug. 5, 2004

(65) Prior Publication Data

US 2006/0074072 A1    Apr. 6, 2006

(30) Foreign Application Priority Data

Jan. 23, 2003    (DE) ................. 103 02 500

(51) Int. Cl.
| | |
|---|---|
| A61K 31/535 | (2006.01) |
| A61K 31/5375 | (2006.01) |
| A61K 31/4965 | (2006.01) |
| A61K 31/4412 | (2006.01) |
| C07D 265/06 | (2006.01) |
| C07D 241/02 | (2006.01) |
| C07D 213/127 | (2006.01) |
| C07D 295/02 | (2006.01) |

(52) U.S. Cl. ............ 514/228.8; 514/237.5; 514/255.06; 514/350; 544/97; 544/175; 544/406; 546/253

(58) Field of Classification Search .............. 514/228.8, 514/237.5, 255.06, 350; 544/97, 175, 406; 546/253

See application file for complete search history.

(56) References Cited

U.S. PATENT DOCUMENTS 7,183,277 B2 * 2/2007 Dorsch et al. ............ 514/231.2
2004/0038858 A1   2/2004 Dorsch et al.

FOREIGN PATENT DOCUMENTS

| WO | WO 02/48099 | 6/2002 | |
|---|---|---|---|
| WO | WO 02/074735 | 9/2002 | |
| WO | WO 02/083630 | 10/2002 | |
| WO | WO 03/093235 | * 11/2003 | ................. 548/200 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*

* cited by examiner

*Primary Examiner*—Kamal A Saeed
*Assistant Examiner*—Samantha L Shterengarts
(74) *Attorney, Agent, or Firm*—Millen, White, Zelano & Branigan, P.C.

(57) ABSTRACT

Novel compounds of the formula (I) in which $R^1$, D, X, W, Y and T have the meaning indicated in Patent Claim (1), e.g. (II), are inhibitors of coagulation factor Xa and can be employed for the prophylaxis and/or therapy of thromboembolic diseases and for the treatment of tumors.

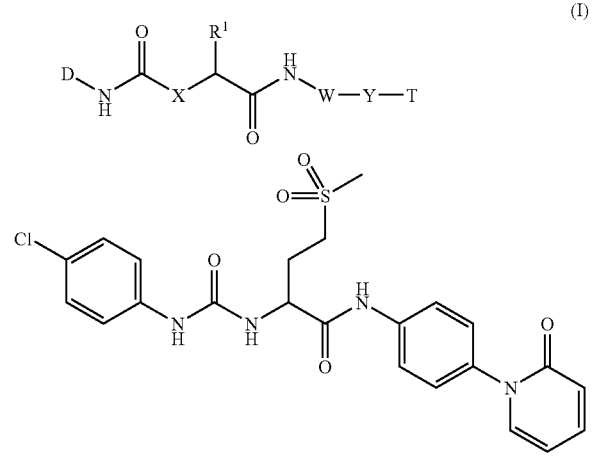

33 Claims, No Drawings

CARBOXAMIDE DERIVATIVES AND THEIR USE AS FACTOR XA INHIBITORS

The invention relates to

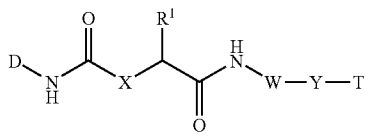

in which

D denotes phenyl or pyridyl, each of which is unsubstituted or mono- or polysubstituted by Hal, A, $OR^2$, $N(R^2)_2$, $NO_2$, CN, $COOR^2$ or $CON(R^2)_2$, $R^1$ denotes A, which is mono-, di- or trisubstituted by $S(O)_mR^2$, $SO_2N(R^2)_2$, $SO_3R^2$, $S(=O)(=NR^2)R^2$, $NR^2SO_2R^2$, $OSO_2R^2$, $OSO_2N(R^2)_2$ or $PO(OR^2)_2$ and may additionally be mono- or disubstituted by $OR^3$, $N(R^3)_2$, CN, $COOR^3$ or $CON(R^3)_2$, $R^2$ denotes H, A, $-[C(R^3)_2]_n$-Ar', $-[C(R^3)_2]_n$-Het', $-[C(R^3)_2]_n$-cycloalkyl, $-[C(R^3)_2]_n$-$N(R^3)_2$ or $-[C(R^3)_2]_n$-$OR^3$, $R^3$ denotes H or A, W denotes $-[C(R^3)_2]_n$-, X denotes $NR^3$ or O, Y denotes alkylene, cycloalkylene, Het-diyl or Ar-diyl, T denotes a mono- or bicyclic saturated, unsaturated or aromatic carbo- or heterocycle having 0 to 4 N, O and/or S atoms, which may be mono-, di- or trisubstituted by =O, $R^2$, Hal, A, $[C(R^3)_2]_n$-Ar, $-[C(R^3)_2]_n$-Het, $-[C(R^3)_2]_n$-cycloalkyl, $OR^2$, $N(R^2)_2$, $NO_2$, CN, $COOR^2$, $CON(R^2)_2$, $NR^2COA$, $NR^2CON(R^2)_2$, $NR^2SO_2A$, $COR^2$, $SO_2NR^2$ and/or $S(O)_nA$, or $N(R^2)_2$ and, if Y=piperidine-1,4-diyl, also $R^2$ or cycloalkyl, A denotes unbranched or branched alkyl having 1-10 C atoms, in which one or two $CH_2$ groups may be replaced by O or S atoms and/or by —CH=CH— groups and/or also 1-7 H atoms may be replaced by F, Ar denotes phenyl, naphthyl or biphenyl, each of which is unsubstituted or mono-, di- or trisubstituted by Hal, A, $OR^2$, $N(R^2)_2$, $NO_2$, CN, $COOR^2$, $CON(R^2)_2$, $NR^2COA$, $NR^2SO_2A$, $COR^2$, $SO_2N(R^2)_2$, $-[C(R^3)_2]_n$-$COOR^2$, $-O-[C(R^3)_2]_o$—$COOR^2$, $SO_3H$ or $S(O)_nA$, Ar' denotes phenyl which is unsubstituted or mono-, di- or trisubstituted by Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$, $S(O)_nA$, $-[C(R^3)_2]_n$-$COOR^3$ or $-O-[C(R^3)_2]_o$—$COOR^3$, Het denotes a mono- or bicyclic saturated, unsaturated or aromatic heterocycle having 1 to 4 N, O and/or S atoms, which may be un-substituted or mono-, di- or trisubstituted by carbonyl oxygen (=O), =S, $=N(R^2)_2$, Hal, A, $-[C(R^3)_2]_n$-Ar, $-[C(R^3)_2]_n$-Het', $-[C(R^3)_2]_n$-cycloalkyl, $-[C(R^3)_2]_n$-$OR^2$, $-[C(R^3)_2]_n$-$N(R^3)_2$, $NO_2$, CN, $-[C(R^3)_2]_n$-$COOR^2$, $-[C(R^3)_2]_n$-$CON(R^2)_2$, $-[C(R^3)_2]_n$-$NR^2COA$, $NR^2CON(R^2)_2$, $-[C(R^3)_2]_n$-$NR^2SO_2A$, $COR^2$, $SO_2N(R^2)_2$ and/or $S(O)_nA$, Het' denotes a mono- or bicyclic saturated, unsaturated or aromatic heterocycle having 1 to 4 N, O and/or S atoms, which may be unsubstituted or mono- or disubstituted by carbonyl oxygen, =S, $=N(R^2)_2$, Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$ and/or $S(O)_nA$, Hal denotes F, Cl, Br or I, m denotes 1 or 2, n denotes 0, 1 or 2, o denotes 1, 2 or 3, and pharmaceutically usable derivatives, salts, solvates and stereoisomers thereof, including mixtures thereof in all ratios.

The invention also relates to the optically active forms, the racemates, the diastereomers and the hydrates and solvates, for example alcoholates, of these compounds.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexy, angina pectoris, restenosis after angioplasty and claudicatio intermittens.

The compounds of the formula I according to the invention are furthermore inhibitors of the coagulation factors factor VIIa, factor IXa and thrombin in the blood coagulation cascade.

Other aromatic amides are described in WO 99/00121 and in WO 00/39118. Aromatic amidine derivatives having an antithrombotic action are disclosed, for example, in EP 0 540 051 B1. Cyclic guanidines for the treatment of thromboembolic diseases are described, for example, in WO 97/08165. Aromatic heterocyclic compounds having factor Xa-inhibitory activity are disclosed, for example, in WO 96/10022. Substituted N—[(aminoiminomethyl)phenylalkyl]azaheterocyclylamides as factor Xa inhibitors are described in WO 96/40679.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example, by the method of G. F. Cousins et al. in *Circulation* 1996, 94, 1705-1712.

Inhibition of factor Xa can thus prevent the formation of thrombin. The compounds of the formula I according to the invention and salts thereof engage in the blood coagulation process by inhibiting factor Xa and thus inhibit the formation of thromboses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example, by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273,12089-12094.

The compounds according to the invention may furthermore be used for the treatment of tumours, tumour diseases and/or tumour metastases. A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59.

The publications listed below describe an antitumoural action of TF-VII and factor Xa inhibitors for various types of tumour:
K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexy, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease. The compounds are also employed in combination with other thrombolytic agents in the case of myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in vivo in patients, or as anticoagulants for the preservation of blood, plasma and other blood products in vitro. The compounds according to the invention are furthermore used for diseases in which blood coagulation makes a crucial contribution to the course of the disease or represents a source of secondary pathology, such as, for example, in cancer, including metastasis, inflammatory diseases, including arthritis, and diabetes.

The compounds according to the invention are furthermore used for the treatment of migraine (F. Morales-Asin et al., Headache, 40, 2000, 45-47).

In the treatment of the diseases described, the compounds according to the invention are also employed in combination with other thrombolytically active compounds, such as, for example, with "tissue plasminogen activator" t-PA, modified t-PA, streptokinase or urokinase. The compounds according to the invention are administered either at the same time as or before or after the other substances mentioned.

Particular preference is given to simultaneous administration with aspirin in order to prevent recurrence of the thrombus formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to claim 1 and salts thereof, characterised in that a) a compound of the formula II

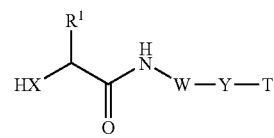

in which
$R^1$, T, W, X and Y have the meaning indicated in claim 1, is reacted with a compound of the formula III

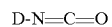

in which
D has the meaning indicated in claim 1, or
b) a compound of the formula IV

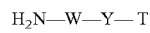

in which W, Y and T have the meaning indicated in claim 1, is reacted with a compound of the formula V

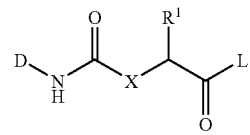

in which
L denotes Cl, Br, I or a free or reactively functionally modified OH group and
$R^1$, X and D have the meanings indicated in claim 1, or
c) a radical $R^1$ is converted into another radical $R^1$ by oxidising the radical $R^1$
and/or a base or acid of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alcoholates.

The term pharmaceutically usable derivatives is taken to mean, for example, the salts of the compounds according to the invention and also so-called prodrug compounds.

The term prod rug derivatives is taken to mean compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals which occur more than once, their meanings are independent of one another.

Above and below, the radicals or parameters $R^1$, D, W, T, X and Y have the meanings indicated under the formula I, unless expressly stated otherwise.

A denotes alkyl, is unbranched (linear) or branched, and has 1, 2, 3, 4, 5, 6, 7, 8, 9 or 10 C atoms. A preferably denotes methyl, furthermore ethyl, 30 propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethyl-propyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methyl propyl, 1-ethyl-2-methylpropyl, 1,1,2- or 1,2,2-trimethylpropyl, furthermore preferably, for example, trifluoromethyl.

A very particularly preferably denotes alkyl having 1-6 C atoms, preferably methyl, ethyl, propyl, isopropyl, butyl, isobutyl, sec-butyl, tert-butyl, pentyl, hexyl or trifluoromethyl.

Cycloalkyl preferably has 3-7 C atoms and denotes cyclopropyl, cyclobutyl, cyclopentyl, cyclohexyl or cycloheptyl.

Hal preferably denotes F, Cl or Br, but also 1.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-hydroxyphenyl, o-, m- or p-nitrophenyl, o-, m- or p-aminophenyl, o-, m- or p-(N-methylamino)phenyl, o-, m- or p-(N-methyl-aminocarbonyl)phenyl, o-, m- or p-acetamidophenyl, o-, m- or p-methoxy-phenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)-phenyl, o-, m- or p-(N-ethylamino)phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methyl-sulfonyl)phenyl, furthermore preferably 2,3-, 2,4-, 2,5-, 2,6-, 3,4- or 3,5-di-fluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro4-chlorophenyl, 3-amino4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or mono-, di- or trisubstituted by Hal, A, $OR^2$, $SO_2A$, $COOR^2$ or CN. Ar particularly preferably denotes, for example, phenyl which is unsubstituted or mono- or disubstituted by Hal, A, OA, $SO_2A$, $SO_2NH_2$, $COOR^2$ or CN, such as, for example, phenyl, 2-methylsulfonylphenyl, 2-aminosulfonylphenyl, 2-, 3- or 4-chlorophenyl, 4-methylphenyl, 4-bromophenyl, 3-fluoro4-methoxyphenyl, 4-trifluoromethoxyphenyl, 4-ethoxyphenyl, 2-methoxyphenyl, 3-cyanophenyl or 4-ethoxycarbonylphenyl. Ar very particularly preferably denotes unsubstituted phenyl, 4-chloro-phenyl or 2-methylsulfonylphenyl.

Unsubstituted Het denotes, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazo-linyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het can thus, for example, also denote 2,3-dihydro-2-, -3-, 4- or -5-furyl, 2,5-dihydro-2-, -3-, 4- or 5-furyl, tetrahydro-2- or -3-furyl, 1,3-dioxolan4-yl, tetrahydro-2- or -3-thienyl, 2,3-dihydro-1-, -2-, -3-, 4- or -5-pyrrolyl, 2,5-dihydro-1-, -2-, -3-, 4- or -5-pyrrolyl, 1-, 2- or 3-pyrrolidinyl, tetrahydro-1-, -2- or 4-imidazolyl, 2,3-dihydro-1-, -2-, -3-, 4- or -5-pyrazolyl, tetrahydro-1-, -3- or 4-pyrazolyl, 1,4-dihydro-1-, -2-, -3- or 4-pyridyl, 1,2,3,4-tetrahydro-1-, -2-, -3-, 4-, -5- or -6-pyridyl, 1-, 2-, 3- or 4-piperidinyl, 2-, 3- or 4-morpholinyl, tetrahydro-2-, -3- or 4-pyranyl, 1,4-dioxanyl, 1,3-dioxan-2-, -4- or -5-yl, hexahydro-1-, -3- or 4-pyridazinyl, hexahydro-1-, -2-, 4- or -5-pyrimidinyl, 1-, 2- or 3-piperazinyl, 1,2,3,4-tetrahydro-1-, -2-, -3-, 4-, -5-, -6-, -7- or -8-quinolyl, 1,2,3,4-tetrahydro-1-, -2-, -3-, 4-, -5-, -6-, -7- or -8-iso-quinolyl, 2-, 3-, 5-, 6-, 7- or 8- 3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4(difluoromethylene-dioxy)phenyl, 2,3-dihydrobenzofuran-5- or 6-yl, 2,3-(2-oxo-methylene-dioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

Het preferably denotes a mono- or bicyclic, saturated, unsaturated or aromatic heterocycle having 1 to 2 N, O and/or S atoms, which may be unsubstituted or mono- or disubstituted by carbonyl oxygen, OH or OA. Het preferably denotes, for example, furyl, thienyl, thiazolyl, imidazolyl, 2,1,3-benzothiadiazolyl, oxazolyl, pyridyl, indolyl, piperidinyl, morpholinyl, tetrahydropyranyl, piperazinyl, pyrazinyl, piperidinyl or pyrrolidinyl, optionally substituted by carbonyl oxygen, such as, for example, 3-oxomorpholin-4-yl, 2-oxopiperidin-1-yl or 2-oxopyrrolidin-1-yl. Het very particularly preferably denotes thienyl, imidazolyl, pyridyl, indolyl, piperidinyl, piperazinyl, 2-oxopiperazinyl, morpholinyl, tetrahydropyran4-yl, 3-oxomorpholin-4-yl, 2-oxo-2H-pyrazin-1-yl, 2-oxopyrrolidin-1-yl or 2-oxopiperidin-1-yl.

Y preferably denotes Het-diyl or Ar-diyl, particularly preferably 1,4-phenylene which is unsubstituted or monosubstituted by A, Cl or F, furthermore also pyridinediyl, preferably pyridine-2,5-diyl or piperidinediyl. Y denotes in particular 1,3- or 1,4-phenylene which is unsubstituted or monosubstituted by methyl, ethyl, propyl, Cl or F.

Y very particularly preferably denotes phenylene which is unsubstituted or monosubstituted by A.

W is preferably absent.

D denotes in particular, for example, phenyl which is unsubstituted or mono- or disubstituted by Hal, A, hydroxyl, methoxy, ethoxy, hydroxy-carbonyl, methoxycarbonyl or ethoxycarbonyl, or pyridyl which is unsubstituted or monosubstituted by Hal.

D very particularly preferably denotes 4-chlorophenyl or 3-chloro-2-pyridyl.

$R^1$ preferably denotes, for example, alkyl having 1, 2, 3, 4, 5 or 6 C atoms which is monosubstituted by $S(O)_mR^2$, $SO_2N(R^2)_2$, $SO_3R^2$, $S(=O)(=NR^2)R^2$, $NR^2SO_2R^2$, $OSO_2R^2$, $OSO_2N(R^2)_2$ or $PO(OR^2)_2$, where $R^2$ preferably denotes, for example, H or alkyl having 1, 2, 3, 4, 5 or 6 C atoms.

$R^2$ preferably denotes, for example, H or alkyl having 1, 2, 3, 4, 5 or 6 C atoms, very particularly preferably H.

$R^3$ preferably denotes, for example, H or alkyl having 1, 2, 3, 4, 5 or 6 C atoms, very particularly preferably H.

n preferably denotes 0 or 1.

m preferably denotes 2.

T preferably denotes a monocyclic saturated or unsaturated heterocycle having 1 to 2 N and/or O atoms, which may be mono- or disubstituted by carbonyl oxygen, OH or OA.

T particularly preferably denotes, for example, piperidin-1-yl, 2-oxo-piperidin-1-yl, 2-oxopyrrolidin-1-yl, pyrrolidin-1-yl, 2-oxo-1H-pyridin-1-yl, 3-oxomorpholin-4-yl, morpholin-4-yl, 4-oxo-1H-pyridin-1-yl, 2,6-dioxo-piperidin1-yl, 2-oxopiperazin-1-yl, 2,6-dioxopiperazin-1-yl, 2,5-dioxo-pyrrolidin-1-yl, 2-oxo-1,3-oxazolidin-3-yl, 3-oxo-2H-pyridazin-2-yl, 2-capro-lactam-1-yl (=2-oxoazepan-1-yl), 2-hydroxy-6-oxopiperazin-1-yl, 2-methoxy-6-oxopiperazin-1-yl, 2-azabicyclo[2.2.2]octan-3-on-2-yl, 5,6-di-hydro-1H-pyrimidin-2-oxo-1-yl, 2-oxo-1,3-oxazinan-3-yl or 4H-1,4-oxazin-4-yl.

Very particular preference is given to 2-oxopiperidin-1-yl, 2-oxopyrrolidin-1-yl, 3-oxomorpholin4-yl, morpholin-4-yl, piperidin-1-yl, pyrrolidin-1-yl or 3-oxo-2H-pyridazin-2-yl.

If Y denotes 1,4-piperidinyl, T is then preferably also, for example, $R^2$, preferably, for example, H or alkyl having 1, 2, 3, 4, 5 or 6 C atoms or cycloalkyl, such as, for example, isopropyl, cyclopentyl or cyclohexyl.

The compounds of the formula I may have one or more chiral centres and therefore occur in various stereoisomeric forms. The formula I covers all these forms.

Accordingly, the invention relates in particular to the compounds of the formula I in which at least one of the said radicals has one of the preferred meanings indicated above. Some preferred groups of compounds may be expressed by the following sub-formulae Ia to In, which conform to the formula I and in which the radicals not designated in greater detail have the meaning indicated under the formula I, but in which in Ia D denotes phenyl which is unsubstituted or mono- or disubstituted by Hal, A, $OR^2$ or $COOR^2$, or pyridyl which is unsubstituted or monosubstituted by Hal;

in Ib D denotes phenyl which is monosubstituted by Hal;

in Ic $R^2$ denotes H or alkyl having 1, 2, 3, 4, 5 or 6 C atoms;

in Id Het denotes a mono- or bicyclic saturated, unsaturated or aromatic heterocycle having 1 to 2 N, O and/or S atoms, which may be unsubstituted or mono- or disubstituted by carbonyl oxygen, OH or OA;

in Ie Y denotes Ar-diyl;

in If Ar denotes phenyl which is unsubstituted or mono-, di- or trisubstituted by Hal, A, $OR^2$, $SO_2A$, $SO_2NH_2$, $COOR^2$ or CN;

in Ig $R^1$ denote alkyl having 1, 2, 3, 4, 5 or 6 C atoms which is monosubstituted by $S(O)_mR^2$, $SO_2N(R^2)_2$, $SO_3R^2$, $S(=O)(=NR^2)R^2$, $NR^2SO_2R^2$, $OSO_2R^2$, $OSO_2N(R^2)_2$ or $PO(OR^2)_2$;

in Ih X denote NH or O;

in Ii T denote a mono- or bicyclic saturated, unsaturated or aromatic heterocycle having 1 to 2 N and/or O atoms, which may be mono- or disubstituted by =O, OH or OA, or $N(R^2)_2$ and, if Y=piperidine-1,4-diyl, also $R^2$ or cycloalkyl;

in Ij Y denotes phenylene which is unsubstituted or monosubstituted by A, in Ik W denotes absent;

in Il D denotes phenyl which is monosubstituted by Hal, $R^1$ denotes alkyl having 1, 2, 3, 4, 5 or 6 C atoms which is monosubstituted by $S(O)_mR^2$, $SO_2N(R^2)_2$, $SO_3R^2$, $S(=O)(=NR^2)R^2$, $NR^2SO_2R^2$, $OSO_2R^2$, $OSO_2N(R^2)_2$ or $PO(OR^2)_2$, $R^2$ denotes H or alkyl having 1, 2, 3, 4, 5 or 6 C atoms, W denotes —$(CH_2)_n$-, X denotes NH or O, Y denotes Ar-diyl, T denotes a mono- or bicyclic saturated, unsaturated or aromatic heterocycle having 1 to 2 N and/or O atoms which is mono- or disubstituted by =O, or $N(R^2)_2$ and, if Y=piperidine-1,4-diyl, also $R^2$ or cycloalkyl, A denotes unbranched or branched alkyl having 1-10 C atoms, in which one or two $CH_2$ groups may be replaced by O or S atoms and/or by —CH=CH— groups and/or also 1-7 H atoms may be replaced by F, Ar denotes phenyl which is unsubstituted or mono-, di- or trisubstituted by Hal, A, $OR^2$, $SO_2A$, $SO_2NH_2$, $COOR^2$ or CN, Hal denotes F, Cl, Br or I, m denotes 1 or 2, n denotes 0, 1 or 2;

in Im D denotes phenyl which is monosubstituted by Hal, $R^1$ denotes alkyl having 1, 2, 3, 4, 5 or 6 C atoms which is monosubstituted by $S(O)_mR^2$, $SO_2N(R^2)_2$, $SO_3R^2$, $S(=O)(=NR)R^2$, $NR^2SO_2R^2$, $OSO_2R^2$, $OSO_2N(R^2)_2$ or $PO(OR^2)_2$, $R^2$ denotes H or alkyl having 1, 2, 3, 4, 5 or 6 C atoms, W denotes —$(CH_2)_n$-, X denotes NH or O, Y denotes Ar-diyl, T denotes piperidin-1-yl, 2-oxopiperidin-1-yl, 2-oxopyrrolidin-1-yl, pyrrolidin-1-yl, 2-oxo-1H-pyridin-1-yl, 3-oxomorpholin-4-yl, morpholin-4-yl, 4-oxo-1H-pyridin-1-yl, 2,6-dioxopiperi-din1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl, 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin4-yl, or $N(R^2)_2$ and, if Y=piperidine-1,4-diyl, also $R^2$ or cycloalkyl, A denotes unbranched or branched alkyl having 1-10 C atoms, in which one or two $CH_2$ groups may be replaced by O or S atoms and/or by —CH=CH— groups and/or also 1-7 H atoms may be replaced by F, Ar denotes phenyl which is unsubstituted or mono-, di- or trisubstituted by Hal, A, $OR^2$, $SO_2A$, $SO_2NH_2$, $COOR^2$ or CN, Hal denotes F, Cl, Br or I, m denotes 1 or 2, n denotes 0, 1 or 2;

in In D denotes phenyl which is monosubstituted by Hal, $R^1$ denotes alkyl having 1, 2, 3, 4, 5 or 6 C atoms which is monosubstituted by $S(O)_mR^2$, $SO_2N(R^2)_2$, $SO_3R^2$, $S(=O)(=NR^2)R^2$, $NR^2SO_2R^2$, $OSO_2R^2$, $OSO_2N(R^2)_2$ or $PO(OR^2)_2$, $R^2$ denotes H or alkyl having 1, 2, 3, 4, 5 or 6 C atoms, W denotes —$(CH_2)_n$-, X denotes NH or O, Y denotes phenylene which is unsubstituted or monosubstituted by A, T denotes piperidin-1-yl, 2-oxopiperidin-1-yl, 2-oxopyrrolidin-1-yl, pyrrolidin-1-yl, 2-oxo-1H-pyridin-1-yl, 3-oxomorpholin-4-yl, morpholin-4-yl, 4-oxo-1H-pyridin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl, 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin4-yl, or $N(R^2)_2$ and, if Y=piperidine-1,4-diyl, also $R^2$ or cycloalkyl, A denotes unbranched or branched alkyl having 1-10 C atoms, in which one or two $CH_2$ groups may be replaced by O or S atoms and/or by —CH=CH— groups and/or also 1-7 H atoms may be replaced by F, Hal denotes F, Cl, Br or I, m denotes 1 or 2, n denotes 0, 1 or 2;

and pharmaceutically usable derivatives, solvates and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

Compounds of the formula I can preferably be obtained by reacting compounds of the formula II with compounds of the formula III.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. The addition of an organic base, such as triethylamine, dimethyl-aniline, pyridine or quinoline, may also be favourable. Depending on the conditions used, the reaction time is between a few minutes and 14 days, and the reaction temperature is between about 0° and 150°, normally between 200 and 130°.

Examples of suitable inert solvents are water; hydrocarbons, such as hexane, petroleum ether, benzene, toluene or xylene; chlorinated hydro-carbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitro-benzene; esters, such as ethyl acetate, or mixtures of the said solvents.

The starting compounds of the formulae II and III are generally known. If they are novel, they can, however, be prepared by methods known per se.

Compounds of the formula I can also be obtained by reacting compounds of the formula IV with compounds of the formula V. In the compounds of the formula V, L preferably denotes Cl, Br, I or a reactively modified OH group, such as, for example, an activated ester, an imidazolide or alkyl-sulfonyloxy having 1-6 C atoms (preferably methylsulfonyloxy or trifluoro-methylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart;). Activated esters are advantageously formed in situ, for example by addition of HOBt or N-hydroxysuccinimide.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. The addition of an organic base, such as triethylamine, dimethylaniline, pyridine or quinoline, or an excess of the amine component of the formula IV may also be favourable. Depending on the conditions used, the reaction time is between a few minutes and 14 days, the reaction temperature is between about 0° and 150°, normally between 20° and 130°. Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Compounds of the formula I can also be obtained by liberating compounds of the formula I from one of their functional derivatives by treatment with a solvolysing or hydrogenolysing agent.

Preferred starting materials for the solvolysis or hydrogenolysis are those which conform to the formula 1, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxy-protecting group instead of the H atom of a hydroxyl group, for example those which conform to the formula I, but carry a —COOR" group, in which R" denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The term "acyl group" is to be understood in the broadest sense in connection with the present process. It encompasses acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl and tolyl; aryloxy-alkanoyl, such as POA; alkoxycarbonyl, such as methoxycarbonyl, ethoxy-carbonyl, 2,2,2-trichloroethoxycarbonyl, BOC (tert-butoxycarbonyl), 2-iodo-ethoxycarbonyl; aralkoxycarbonyl, such as CBZ ("carbobenzoxy"), 4-methoxybenzyloxycarbonyl, FMOC; arylsulfonyl, such as Mtr. Preferred amino-protecting groups are BOC and Mtr, furthermore CBZ, Fmoc, benzyl and acetyl.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 300 (room temperature).

The BOC, OBut and Mtr groups can, for example, preferably be cleaved off using TFA in dichloromethane or using approximately 3 to 5N HCl in dioxane at 15-300, the FMOC group can be cleaved off using an approximately 5 to 50% solution of dimethylamine, diethylamine or piperidine in DMF at 15-30°.

Protecting groups which can be removed hydrogenolytically (for example CBZ, benzyl or the liberation of the amidino group from its oxadiazole derivative)) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, N-methyl-pyrrolidone (NMP) or dimethylformamide (DMF); nitriles, such as aceto-nitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The biphenyl-$SO_2NH_2$ group is preferably employed in the form of its tert-butyl derivative. The tert-butyl group is cleaved off, for example, using TFA with or without addition of an inert solvent, preferably with addition of a small amount of anisole (1-10% by volume).

It is furthermore possible to convert a compound of the formula I into another compound of the formula I by converting one or more $R^1$, D, E and/or W radical(s) into one or more $R^1$, D, Y, and/or T radical(s), for example by acylating an amino group or reducing nitro groups to amino groups (for example by hydrogenation on Raney nickel or Pd/carbon in an inert solvent, such as methanol or ethanol).

Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

If Y denotes 1,4-piperidinyl, the alkylation of the piperidine nitrogen can be carried out by conventional methods of reductive amination.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

It is also possible to use physiologically acceptable organic bases, such as, for example, ethanolamine.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of pharmaceutical compositions, in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

These medicaments can be used in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, suitable for topical application are ointments, creams or powders or also as nasal sprays. The novel compounds may also be lyophilised and the resultant lyophilisates used, for example, to prepare injection preparations. The compositions indicated may be sterilised and/or comprise adjuvants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

The compounds of the formula I and physiologically acceptable salts thereof can be used for combating and preventing thromboembolic diseases, such as thrombosis, myocardial infarction, arteriosclerosis, inflammation, apoplexy, angina pectoris, restenosis after angioplasty, claudicatio intermittens, tumours, tumour diseases and/or tumour metastases.

In general, the substances according to the invention are preferably administered here in doses between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules each containing an effective amount of a compound of the formula I and/or pharmaceutically usable derivatives, solvates and stereo-isomers thereof, including mixtures thereof in all ratios, and an effective amount of a further medicament active ingredient in dissolved or lyophilised form.

The invention furthermore relates to the use of compounds of the formula I and/or pharmaceutically usable derivatives, solvates and stereoisomers thereof, including mixtures thereof in all ratios, for the preparation of a medicament for the treatment of thromboses, myocardial infarction, arteriosclerosis, inflammation, apoplexy, angina pectoris, restenosis after angioplasty, claudicatio intermittens, migraine, tumours, tumour diseases and/or tumour metastases, in combination with at least one further medicament active ingredient.

Above and below, all temperatures are given in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M+ESI (electrospray ionisation) (M+H)+FAB (fast atom bombardment) (M+H)+

EXAMPLE 1

The preparation of 2-[3-(4-chlorophenyl)ureido]-N-[4-(2-oxo-2H-pyridin-1-yl)phenyl]-4-methanesulfonylbutyramide is carried out analogously to the following scheme:

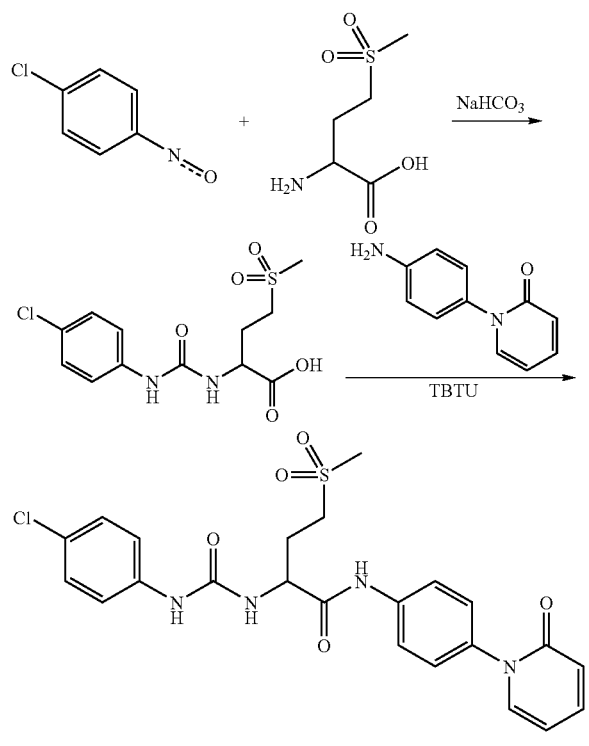

1.1 A solution of 9.24 g (110 mmol) of sodium hydrogencarbonate and 5.0 g (27.6 mmol) of 2-amino4-methanesulfonylbutyric acid in 50 ml of water is heated to 80° C., and 8.45 g (55.0 mmol) of 4-chlorophenyl isocyanate is added. The reaction mixture is stirred at this temperature for 1 hour. The mixture is allowed to cool, and the precipitate formed is filtered off. The filtrate is acidified using 1N HCl, and the precipitate formed is filtered off and dried: 2-[3-(4-chlorophenyl)ureido]-4-methanesulfonylbutyric acid as colourless solid; ESI 335.

1.2 209 mg (0.650 mmol) of [(benzotriazol-1-yloxy)dimethylamino-methylene]dimethylammonium tetrafluoroborate (TBTU) are added to a solution of 167 mg (0.500 mmol) of 2-[3-(4-chlorophenyl)ureido]4-methanesulfonylbutyric acid and 93.1 mg (0.500 mmol) of 1-(4-amino-phenyl)-1H-pyridin-2-one in 1 ml of DMF, and the mixture is stirred at room temperature for 24 hours. The reaction mixture is added to saturated sodium hydrogencarbonate solution, the precipitate formed is filtered off and dried: 2-[3-(4-chlorophenyl)ureido]-N-[4-(2-oxo-2H-pyridin-1-yl)phenyl]-4-methanesulfonylbutyramide ("1A") as colourless solid; ESI 503.

The following compounds are obtained analogously
2-[3-(4-chlorophenyl)ureido]-N-[4-(2-oxo-2H-pyrazin-1-yl)phenyl]-4-methanesulfonylbutyramide ("1B"), ESI 504;
2-[3-(4-chlorophenyl)ureido]-N-[4-(3-oxomorphin-4-yl)phenyl]-4-methanesulfonylbutyramide ("1C"), ESI 509;
(R)-2-[3-(4-chlorophenyl)ureido]-N-[4-(3-oxomorpholin4-yl)phenyl]-4-methanesulfonylbutyramide ("2C"), ESI 509;
(R)-2-[3-(4-chlorophenyl)ureido]-N-[4-(2-oxo-2H-pyridin-1-yl)phenyl]-4-methanesulfonylbutyramide ("2D"), ESI 503;
(R)-2-[3-(4-chlorophenyl)ureido]-N-[3-methyl-4-(3-oxomorpholin4-yl)-phenyl]4-methanesulfonylbutyramide ("1C"), ESI 523;

EXAMPLE 2

The preparation of (R)-2-[3-(4-chlorophenyi)ureido]-N-[4-(2-oxo-2H-pyridin-1-yl)phenyl]-3-methanesulfonylpropionamide is carried out analogously to the following scheme:

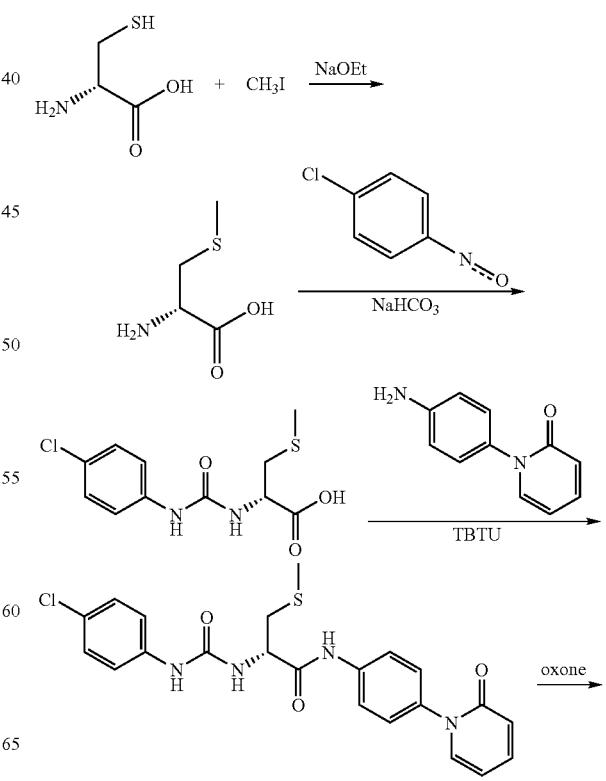

-continued

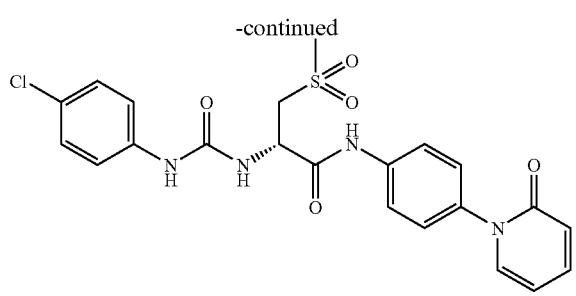

2.1 13.0 g (565 mmol) of sodium are added little by little with stirring to a suspension of 25 g (142 mmol) of D-cysteine hydrochloride hydrate in 350 ml of ethanol. When the sodium has dissolved, 10.0 ml (160 mmol) of methyl iodide is added dropwise. After stirring at room temperature for a further 30 min, water is added to the reaction mixture until a clear solution forms. Acetic acid is then added until a pH of 6 has been reached. The reaction mixture is evaporated under reduced pressure to a volume of about 200 ml and cooled to 5° C. The precipitate formed is filtered off: (R)-2-amino-3-methylsulfanylpropionic acid mixed with sodium acetate (weight ratio 35:65) as colourless solid; ESI 136.

2.2 A solution of 18.0 g (214 mmol) of sodium hydrogencarbonate and 13.8 g (35.7 mmol) of 35% (R)-2-amino-3-methylsulfanylpropionic acid in 200 ml of water is heated to 80° C., and 11.0 g (71.6 mmol) of 4-chloro-phenyl isocyanate is added. The reaction mixture is stirred at this temperature for 1 hour. The mixture is allowed to cool, and the precipitate formed is filtered off. The filtrate is acidified using 1N HCl, and the precipitate formed is filtered off and dried: (R)-2-[3-(4-chlorophenyl)ureido]-3-methyl-sulfanylpropionic acid as slightly greenish solid; ESI 289.

2.3 1.440 g (4.49 mmol) of [(benzotriazol-1-yloxy)dimethylamino-methylene]dimethylammonium tetrafluoroborate (TBTU) are added to a solution of 1.00 g (3.46 mmol) : of (R)-2-[3-(4-chlorophenyl)ureido]-3-methylsulfanylpropionic acid and 640 mg (3.44 mmol) of 1-(4-amino-phenyl)-1H-pyridin-2-one in 5 ml of DMF, and the mixture is stirred at room temperature for 24 hours. The reaction mixture is added to saturated sodium hydrogencarbonate solution, and the precipitate formed is filtered off and dried: (R)-2-[3-(4-chlorophenyl)ureido]-3-methylsulfanyl-N-[4-(2-oxo-2H-pyridin-1-yl)phenyl]propionamide as colourless solid; ESI 457.

2.4 A solution of 400 mg of oxone in 6 ml of water is added to a solution of 200 mg (0.438 mmol) of (R)-2-[3-(4-chlorophenyl)ureido]-3-methyl-sulfanyl-N-[4-(2-oxo-2H-pyridin-1-yl)phenyl]propionamide in 10 ml of methanol, and the reaction mixture is stirred at room temperature for 48 hours. The reaction mixture is added to water, and the precipitate formed is filtered off and dried: (R)-2-[3-(4-chlorophenyl)ureido]-N-[4-(2-oxo-2H-pyridin-1-yl)phenyl]-3-methanesulfonylpropionamide as colourless solid ("2A"); ESI 489.

The following compounds are obtained analogously (S)-2-[3-(4-chlorophenyl)ureido]-N-[4-(2-oxo-2H-pyridin-1-yl)phenyl]-3-methanesulfonylpropionamide, (S)-2-[3-(4-chlorophenyl)ureido]-N-[4-(3-oxomorpholin-4-yl)phenyl]-3-methanesulfonylpropionamide, ("2B"), ESI 495;

(R)-2-[3-(4-chlorophenyl)ureido]-N-[3-methyl-4-(3-oxo-morpholin4-yl)-phenyl]-3-methanesulfonylpropionamide, ESI 509;

(R)-2-[3-(4-chlorophenyl)ureido]-N-[4-(2-oxo-1,3-oxazinan-3-yl)-phenyl]-3-methanesulfonylpropionamide, ESI 495.

EXAMPLE 3

The preparation of (R)-2-[N-(4-chlorophenyl)carbamoyloxy]-N-[4-(3-oxo-morpholin-4-yl)phenyl]-3-methanesulfonylpropionamide is carried out analogously to the following scheme:

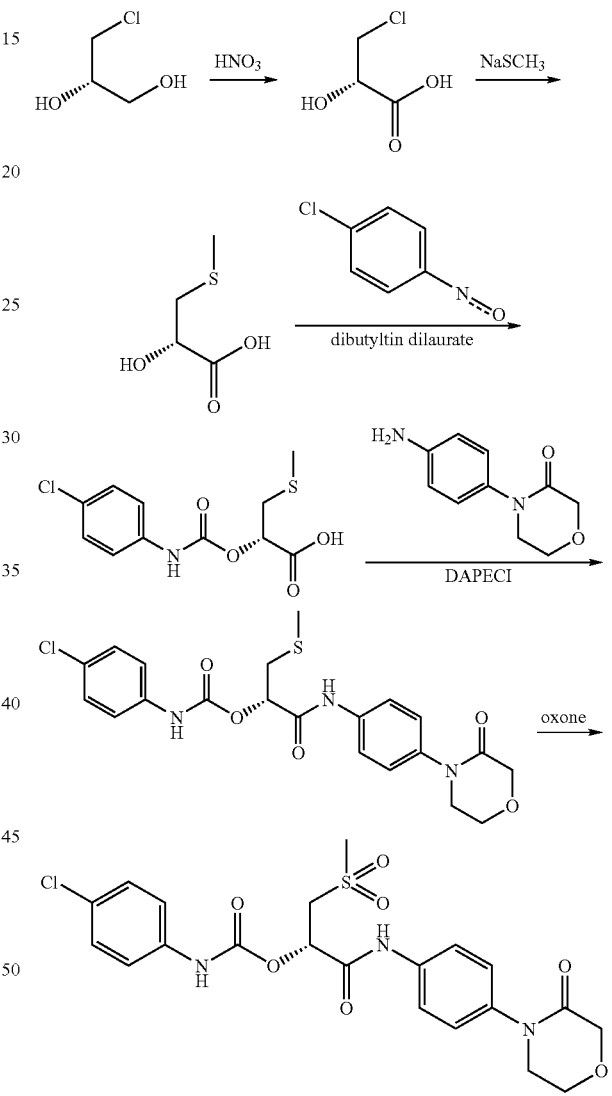

3.1 24 g (217 mmol) of (S)-3-chloro-1,2-propanediol is dissolved in 60 ml of 65% nitric acid held at 0° C. The solution is heated at 70° C. for 30 min and subsequently at 100° C. for 15 min. The reaction mixture is allowed to cool, 15 g of sodium hydrogencarbonate are added, and the mixture is extracted with tert-butyl methyl ether. The organic phase is dried over sodium sulphate and evaporated, and the residue is recrystallised from chloroform: (R)-3-chloro-2-hydroxypropionic acid as colourless needles of melting point 93° C., ESI 125.

3.2 11.2 g (160 mmol) of sodium methanethiolate are added to a solution of 5.00 g (40.2 mmol) of (R)-3-chloro-2-hydroxypropionic acid in 80 ml of methanol, and the mixture is heated at the boil for 18 hours. The reaction mixture is filtered, and the filtrate is evaporated. The residue is acidified using 2N HCl and extracted with ethyl acetate. The organic phase is evaporated: (R)-2-hydroxy-3-methylsulfanylpropionic acid as yellowish oil; ESI 137.

3.3 400 mg (0.63 mmol) of dibutyltin dilaurate are added to a solution of 3.70 g (27.2 mmol) of (R)-2-hydroxy-3-methylsulfanylpropionic acid and 4.18 g (27.2 mmol) of 4-chlorophenyl isocyanate in 50 ml of dichloro-methane, and the mixture is stirred at room temperature for 24 hours. The reaction mixture is added to water and extracted with ethyl acetate. The organic phase is evaporated: (R)-2-(4-chlorophenylcarbamoyloxy)-3-methylsulfanylpropionic acid as colourless solid; ESI 290.

3.4 A solution of 1.00 g (3.45 mmol) of (R)-2-(4-chlorophenylcarbamoyloxy)-3-methylsulfanylpropionic acid, 663 mg (3.45 mmol) of 4-(4-aminophenyl)morpholin-3-one and 863 mg (4.50 mmol) of N-(3-dimethyl-aminopropyl)-N'-ethylcarbodiimide hydrochloride (DAPECI) in 3 ml of DMF is stirred at room temperature for 24 hours. The reaction mixture is added to saturated sodium hydrogencarbonate solution, and the precipitate formed is filtered off: (R)-2-[N-(4-chlorophenyl)carbamoyloxy]-N-[4-(3-oxo-morpholin-4-yl)phenyl]-3-methanesulfanylpropionamide as colourless solid; ESI 464.

3.5 A solution of 2.7 g of oxone in 30 ml of water is added to a solution of 775 mg (1.67 mmol) of 2-methylsulfanyl-1-[4-(3-oxomorpholin4-yl)-phenylcarbamoyl]ethyl (R)-(4-chlorophenyl)carbamate in 50 ml of methanol, and the reaction mixture is stirred at room temperature for 24 hours. The reaction mixture is added to water, and the precipitate formed is filtered off and dried: (R)-2-[N-(4-chlorophenyl)carbamoyloxy]-N-[4-(3-oxo-morpholin4-yl)phenyl]-3-methanesulfonylpropionamide ("1C") as colourless solid; ESI 496.

The following are obtained analogously (S)-2-[N-(4-chlorophenyl)carbamoyloxy]-N-[3-oxomorpholin4-yl)-phenyl]-3-methanesulfonylpropionamide, 2-[N-(4-chlorophenyl)carbamoyloxy]-N-[4-(2-oxo-2H-pyridin-1-yl)-phenyl]-3-methanesulfonylpropionamide, ESI 490.

EXAMPLE 4

The preparation of 2-[3-(4-chlorophenyl)ureido]-N-[4-(3-oxomorpholin-4-yl)-phenyl]-3-sulfopropionamide is carried out analogously to the following scheme:

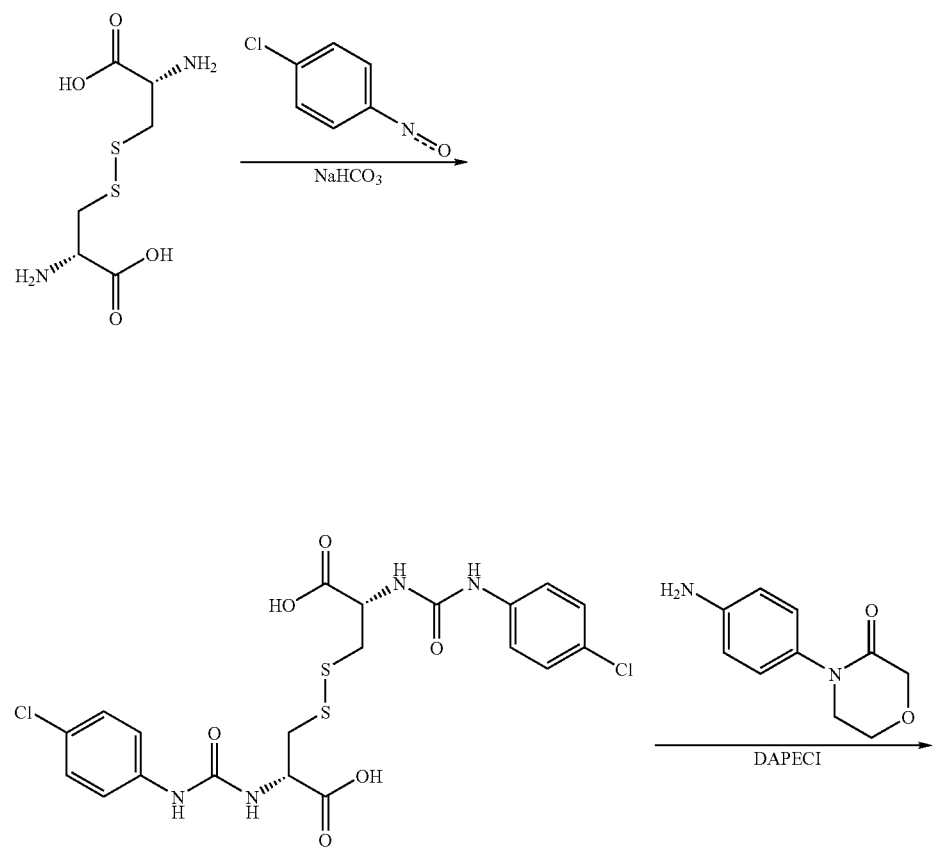

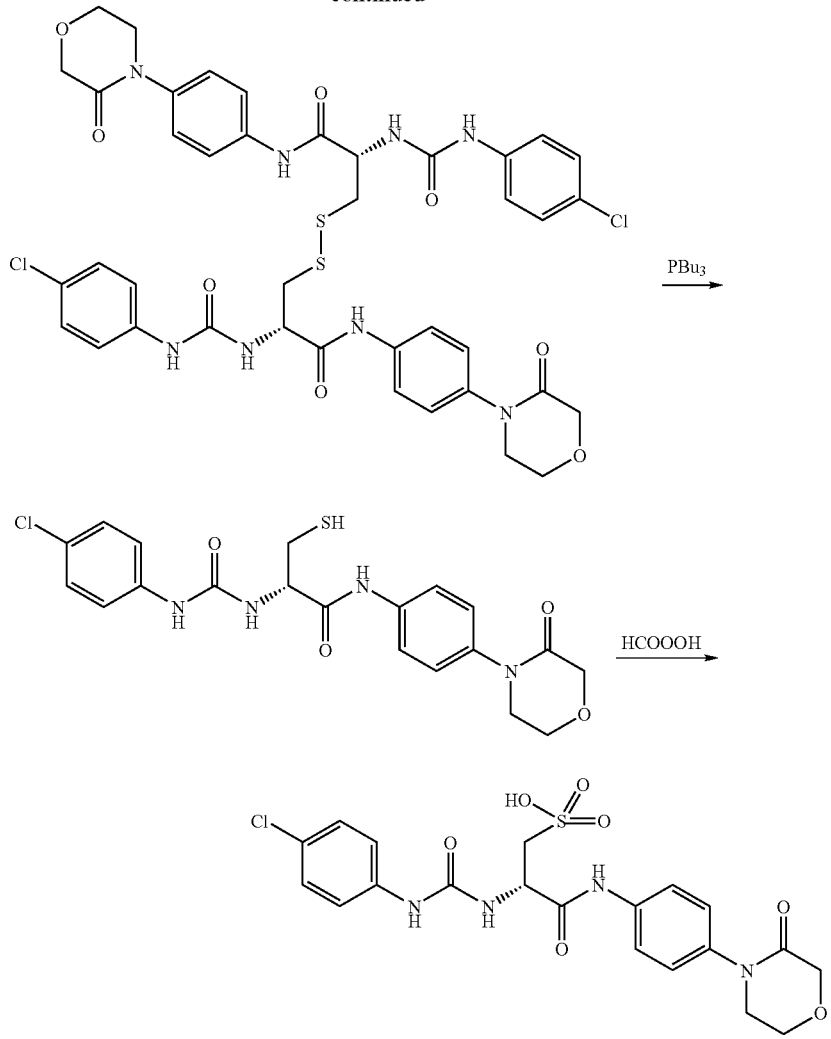
2-[3-(4-Chlorophenyl)ureido]-N-[4-(2-oxo-2H-pyridin-1-yl)phenyl]-3-sulfo-propionamide is obtained analogously.
EXAMPLE 5
The preparation of 2-[3-(4-chlorophenyl)ureido]-N-[4-(2-oxopiperidin-1-yl)-phenyl]-3-(dimethoxyphosphoryl)propionamide is carried out analogously to the following scheme:
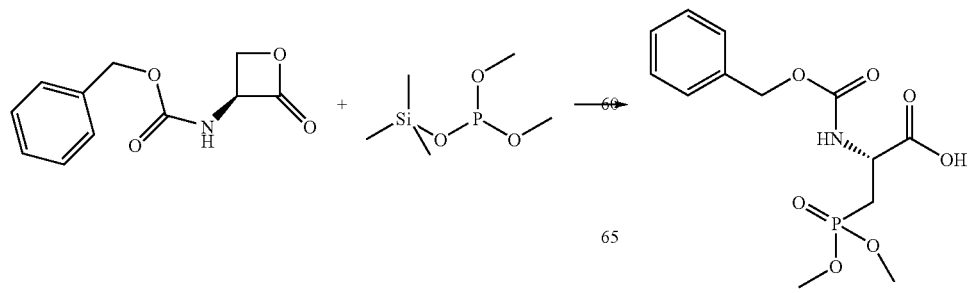

-continued

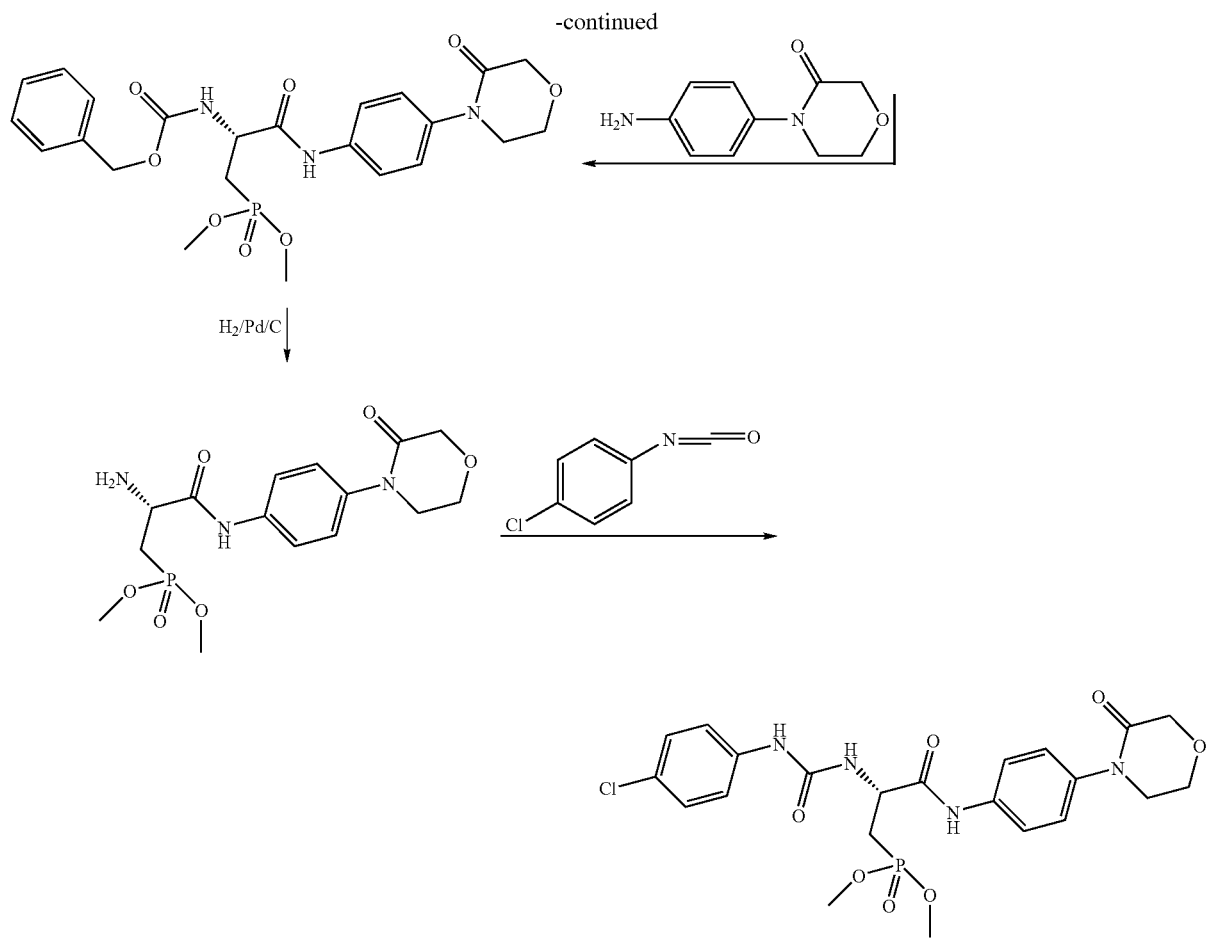

5.1 Analogously to the literature (Lohse, P. A., Felber, R., Tetrahedron Lett., 39; (1998); 2067-2070), 0.5 g (64.2%) of (S)-2-benzyloxycarbonyl-amino-3-(dimethoxyphosphoryl) propionic acid is obtained as colourless oil, ESI 331, from 0.5 g (2.26 mmol) of N-benzyloxycarbonyl-L-serine β-lactone and 5 ml of dimethyltrimethylsilyl phosphite.

5.2 Analogously to Example 3, 3.4, 0.4 g (53.2%) of (S)-2-(benzyloxy-carbonylamino)-N-[4-(3-oxomorpholin-4-yl) phenyl]-3-(dimethoxyphosphoryl)propionamide is obtained as colourless oil, ESI 505, from 0.48 g (1.45 mmol) of (S)-2-benzyloxycarbonylamino-3-(dimethoxyphosphoryl)-propionic acid and 0.28 g (1.45 mmol) of 4-(4-aminophenyl)morpholin-3-one.

5.3 The mixture of 0.39 g (0.78 mmol) of (S)-2-(benzyloxycarbonyl-amino)-N-[4-(3-oxomorpholin-4-yl)phenyl]-3-(dimethoxyphosphoryl)-propionamide and 0.4 g of 5% palladium/carbon in 30 ml of methanol is hydrogenated until hydrogen is no longer taken up. The reaction mixture is subsequently filtered off, and the filtrate is evaporated to dryness, giving 0.27 g of (S)-2-amino-N-[4-(3-oxomorpholin-4-yl) phenyl]-3-(dimethoxyphosphoryl)propionamide as colourless oil, ESI 371.

5.4 The solution of 0.2 g (0.54 mmol) of dimethyl (S)-{2-amino-2-[4-(3-oxomorpholin-4-yl)phenylcarbamoyl] ethyl}phosphonate and 0.092 g (0.54 mmol) of 4-chlorophenyl isocyanate in 10 ml of dichloromethane is stirred at room temperature for 12 hours. The methylene chloride solution is subsequently washed successively with 10 ml of each of 1N hydrochloric acid, saturated sodium hydrogencarbonate solution and water and dried over sodium sulfate. After the solvent has been stripped off, 10 ml of diethyl ether are added to the residue, and the white precipitate deposited is filtered off, giving 0.28 g (100%) of (S)-2-[3-(4-chlorophenyl)ureido]-N-[4-(3-oxomorpholin-4-yl)phenyl]-3-(dimethoxyphosphoryl) propionamide ("1D"), ESI 525.

(R)-2-[3-(4-Chlorophenyl)ureido]-N-[4-(3-oxomorpholin-4-yl)phenyl]-3-(dimethoxyphosphoryl)propionamide, ESI 525; (R)-2-[3-(4-chlorophenyl)ureido]-N-[3-methyl-4-(3-oxomorpholin-4-yl)-phenyl]-3-(dimethoxyphosphoryl) propionamide, ESI 539 and (S)-2-[3-(4-chlorophenyl)ureido]-N-[3-methyl-4-(3-oxomorpholin-4-yl)-phenyl]-3-(dimethoxyphosphoryl)propionamide, ESI 539 are obtained correspondingly.

2-[3-(4-Chlorophenyl)ureido]-N-[4-(2-oxopiperidin-1-yl) phenyl]-3-(di-methoxyphosphoryl)propionamide is obtained analogously.

Hydrolysis thereof gives 2-[3-(4-chlorophenyl)ureido]-N-[4-(3-oxomorpholin4-yl)phenyl]-3-phosphonopropionamide.

EXAMPLE 6

The preparation of 2-[3-(4-chlorophenyl)ureido]-N-[4-(3-oxomorpholin4-yl)phenyl]4-(methanesulfoximinyl)butyramide is carried out analogously to the following scheme:

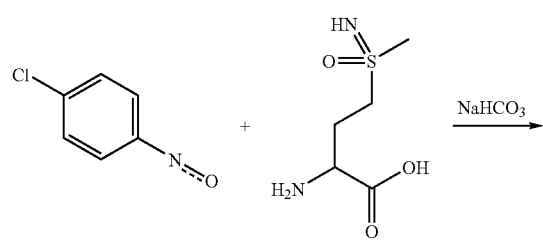

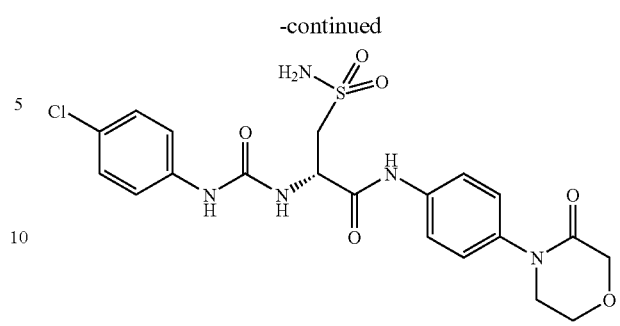

2-[3-(4-Chlorophenyl)ureido]-N-[4-(2-oxo-2H-pyridin-1-yl)phenyl]-3-sulfamoylpropionamide is obtained analogously.

EXAMPLE 8

The preparation of 2-[3-(4-chlorophenyl)ureido]-N-[4-(3-oxomorpholin-4-yl)-phenyl]-3-methanesulfonylaminopropionamide is carried out analogously to the following scheme:

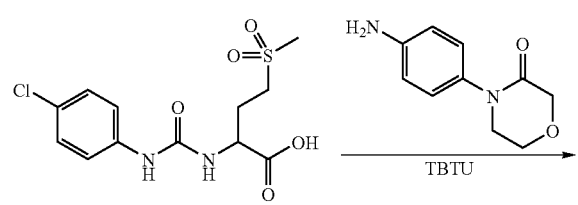

EXAMPLE 7

The preparation of 2-[3-(4-chlorophenyl)ureido]-N-[4-(3-oxomorpholin4-yl)-phenyl]-3-sulfamoylpropionamide is carried out analogously to the following scheme:

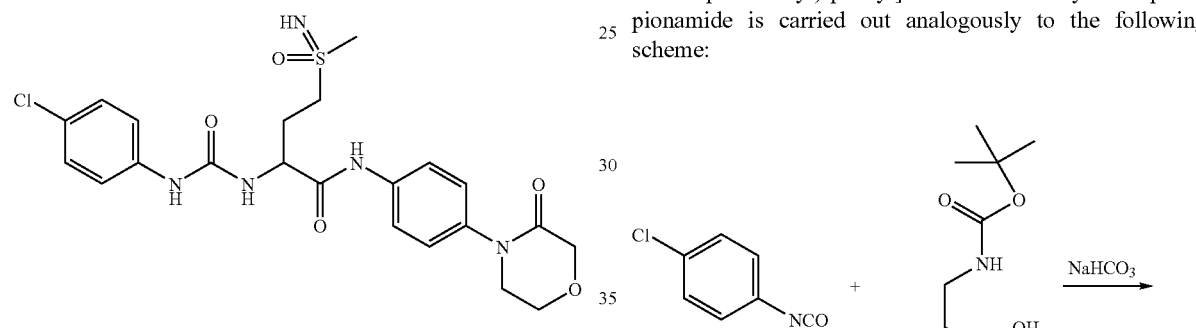

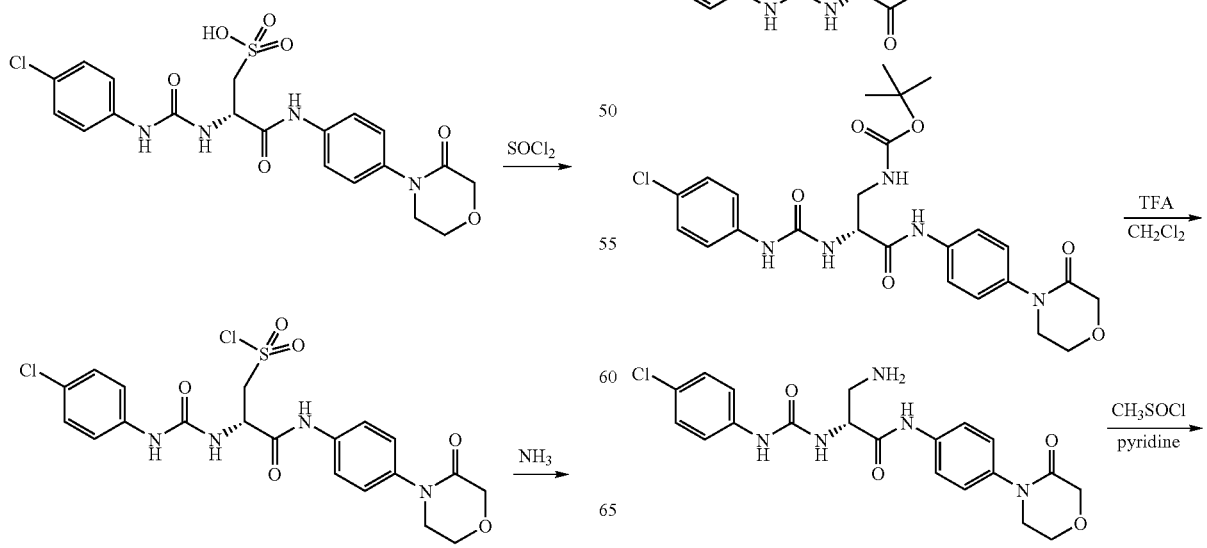

-continued

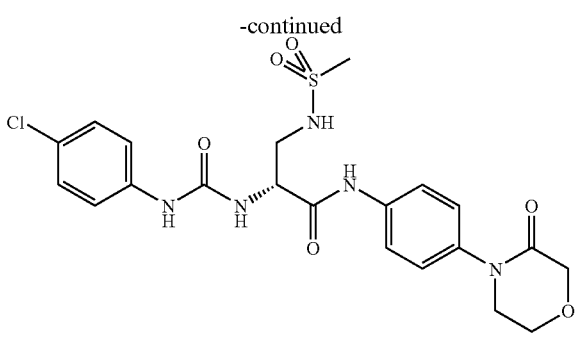

The compound
(R)-2-[3-(4-chlorophenyl)ureido]-N-[4-(3-oxomorpholin-4-yl)phenyl]-5-methanesulfonylaminovaleramide, ESI 552, is obtained analogously.

EXAMPLE 9

The preparation of 2-[3-(4-chlorophenyl)ureido]-N-[4-(3-oxomorpholin-4-yl)-phenyl]-3-sulfamoyloxypropionamide

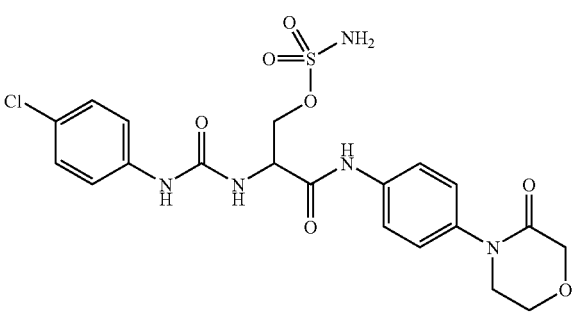

can be carried out by reaction of the hydroxyl derivative with chlorosulfonyl isocyanate.
(R)-2-[3-(4-Chlorophenyl)ureido]-N-[4-(3-oxomorpholin-4-yl)phenyl]-3-sulfamoyloxypropionamide, ESI 512, is obtained correspondingly.

Pharmacological Data (Affinity to Receptors)

| Compound No. | FXa-IC$_{50}$ [M] | TF/FVIIa-IC$_{50}$ [M] |
|---|---|---|
| "1A" | $2.8 \times 10^{-8}$ | $2.8 \times 10^{-8}$ |
| "1B" | $4.2 \times 10^{-8}$ | $4.3 \times 10^{-8}$ |
| "1C" | $5.9 \times 10^{-8}$ | $5.8 \times 10^{-8}$ |
| "2A" | $6.4 \times 10^{-9}$ | $1.2 \times 10^{-8}$ |
| "1C" | $1.1 \times 10^{-8}$ | $2.3 \times 10^{-8}$ |
| "1D" | $8.5 \times 10^{-8}$ | |

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

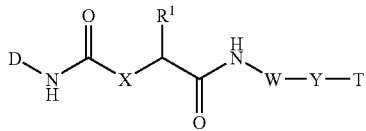

in which
D denotes phenyl or pyridyl, each of which is unsubstituted or mono- or polysubstituted by Hal, A, $OR^2$, $N(R^2)_2$, $NO_2$, CN, $COOR^2$ or $CON(R^2)_2$,
$R^1$ denotes A, which is mono-, di- or trisubstituted by $S(=O)(=NR^2)R^2$, $NR^2SO_2R^2$, $OSO_2R^2$, $OSO_2N(R^2)_2$ or $PO(OR^2)_2$, and may additionally be mono- or disubstituted by $OR^3$, $N(R^3)_2$, CN, $COOR^3$ or $CON(R^3)_2$, and may additionally be mono-, di- or trisubstituted by $S(O)_mR^2$, $SO_2N(R^2)_2$, or $SO_3R^2$,
$R^2$ denotes H, A, $-[C(R^3)_2]_n-Ar'$, $-[C(R^3)_2]_n$-Het', $-[C(R^3)_2]_n$cycloalkyl, $-[C(R^3)_2]_n-N(R^3)_2$ or $[C(R^3)_2]_n-OR^3$,
$R^3$ denotes H or A,
W denotes $-[C(R^3)_2]_n-$,
X denotes $NR^3$ or O,
Y denotes alkylene, cycloalkylene, Het-diyl or Ar-diyl,
T denotes a mono- or bicyclic saturated, unsaturated or aromatic carbo- or heterocycle having 0 to 4 N, O and/or S atoms, which may be mono-, di- or trisubstituted by =O, $R^2$, Hal, A, $-[C(R^3)_2]_n-Ar$, $-[C(R^3)_2]_n$-Het, $-[C(R^3)_2]_n$-cycloalkyl, $OR^2$, $N(R^2)_2$, $NO_2$, CN, $COOR^2$, $CON(R^2)_2$, $NR^2COA$, $NR^2CON(R^2)_2$, $NR^2SO_2A$, $COR^2$, $SO_2NR^2$ and/or $S(O)_nA$, or $N(R^2)_2$
and, if Y=piperidine-1,4-diyl, also $R^2$ or cycloalkyl,
A denotes unbranched or branched alkyl having 1-10 C atoms, in which one or two $CH_2$ groups may be replaced by O or S atoms and/or by $-CH=CH-$ groups and/or also 1-7 H atoms may be replaced by F,
Ar denotes phenyl, naphthyl or biphenyl, each of which is unsubstituted or mono-, di- or trisubstituted by Hal, A, $OR^2$, $N(R^2)_2$, $NO_2$, CN, $COOR^2$, $CON(R^2)_2$, $NR^2COA$, $NR^2SO_2A$, $COR^2$, $SO_2N(R^2)_2$, $-[C(R^3)_2]_n-COOR^2$, $-O-[C(R^3)_2]_o-COOR^2$, $SO_3H$ or $S(O)_nA$,
Ar' denotes phenyl which is unsubstituted or mono-, di- or trisubstituted by Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$, $S(O)_nA$, $-[C(R^3)_2]_n-COOR^3$ or $-O-[C(R^3)_2]_o-COOR^3$,
Het denotes a mono- or bicyclic saturated, unsaturated or aromatic heterocycle having 1 to 4 N, O and/or S atoms, which may be unsubstituted or mono-, di- or trisubstituted by carbonyl oxygen (=O), =S, $=N(R^2)_2$, Hal, A, $-[C(R^3)_2]_n-Ar$, $-[C(R^3)_2]_n$-Het', $-[C(R^3)_2]_n$-cycloalkyl, $-[C(R^3)_2]_n-OR^2$, $-[C(R^3)_2]_n-N(R^3)_2$, $NO_2$, CN, $-[C(R^3)_2]_n-COOR^2$, $-[C(R^3)_2]_n-CON(R^2)_2$, $-[C(R^3)_2]_n-NR^2COA$, $NR^2CON(R^2)_2$, $-[C(R^3)_2]_n-NR^2SO_2A$, $COR^2$, $SO_2N(R^2)_2$ and/or $S(O)_nA$,
Het' denotes a mono- or bicyclic saturated, unsaturated or aromatic heterocycle having 1 to 4 N, O and/or S atoms, which may be unsubstituted or mono- or disubstituted by carbonyl oxygen, =S, $=N(R^2)_2$, Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$ and/or $S(O)_nA$, Hal denotes F, Cl, Br or I,
m denotes 1 or 2,
n denotes 0, 1 or 2, and
o denotes 1, 2 or 3,
or a pharmaceutically acceptable salt or stereoisomer thereof.
2. A compound according to claim 1, in which
D denotes phenyl which is unsubstituted or mono- or disubstituted by Hal, A, $OR^2$ or $COOR^2$, or pyridyl which is unsubstituted or monosubstituted by Hal.
3. A compound according to claim 1, in which
D denotes phenyl which is monosubstituted by Hal.
4. A compound according to claim 1, in which
$R^2$ denotes H or alkyl having 1, 2, 3, 4, 5 or 6 C atoms.
5. A compound according to claim 1, in which
Het denotes a mono- or bicyclic saturated, unsaturated or aromatic heterocycle having 1 to 2 N, O and/or S atoms, which may be unsubstituted or mono- or disubstituted by carbonyl oxygen, OH or OA.
6. A compound according to claim 1, in which
Y denotes Ar-diyl.
7. A compound according to claim 1, in which
Ar denotes phenyl which is unsubstituted or mono-, di- or trisubstituted by Hal, A, $OR^2$, $SO_2A$, $SO_2NH_2$, $COOR^2$ or CN.
8. A compound according to claim 1, in which
$R^1$ denotes alkyl having 1, 2, 3, 4, 5 or 6 C atoms which is monosubstituted by $S(=O)(=NR^2)R^2$, $NR^2SO_2R^2$, $OSO_2R^2$, $OSO_2N(R^2)_2$ or $PO(OR^2)_2$.
9. A compound according to claim 1, in which
X denotes NH or O.
10. A compound according to claim 1, in which
T denotes a mono- or bicyclic saturated, unsaturated or aromatic heterocycle having 1 to 2 N and/or O atoms, which may be mono- or disubstituted by =O, OH or OA, or $N(R^2)_2$
and, if Y=piperidine-1,4-diyl, also $R^2$ or cycloalkyl.
11. A compound according to claim 1, in which
Y denotes phenylene which is unsubstituted or monosubstituted by A.
12. A compound according to claim 1, in which
n is 0.
13. A compound according to claim 1, in which
D denotes phenyl which is monosubstituted by Hal,
$R^1$ denotes alkyl having 1, 2, 3, 4, 5 or 6 C atoms which is monosubstituted by $S(=O)(=NR^2)R^2$, $NR^2SO_2R^2$, $OSO_2R^2$, $OSO_2N(R^2)_2$ or $PO(OR^2)_2$,
$R^2$ denotes H or alkyl having 1, 2, 3, 4, 5 or 6 C atoms,
W denotes $-(CH_2)_n-$,
X denotes NH or O,
Y denotes Ar-diyl,
T denotes a mono- or bicyclic saturated, unsaturated or aromatic heterocycle having 1 to 2 N and/or O atoms which is mono- or disubstituted by =O,
or $N(R^2)_2$
and, if Y=piperidine-1,4-diyl, also $R^2$ or cycloalkyl,
A denotes unbranched or branched alkyl having 1-10 C atoms, in which one or two $CH_2$ groups may be replaced by O or S atoms and/or by $-CH=CH-$ groups and/or also 1-7 H atoms may be replaced by F,
Ar denotes phenyl which is unsubstituted or mono-, di- or trisubstituted by Hal, A, $OR^2$, $SO_2A$, $SO_2NH_2$, $COOR^2$ or CN,
Hal denotes F, Cl, Br or I,
m denotes 1 or 2, and
n denotes 0, 1 or 2.

14. A compound according to claim 1, in which

D denotes phenyl which is monosubstituted by Hal, $R^1$ denotes alkyl having 1, 2, 3, 4, 5 or 6 C atoms which is monosubstituted by $S(=O)(=NR^2)R^2$, $NR^2SO_2R^2$, $OSO_2R^2$, $OSO_2N(R^2)_2$ or $PO(OR^2)_2$, $R^2$ denotes H or alkyl having 1, 2, 3, 4, 5 or 6 C atoms, W denotes —$(CH_2)_n$—, X denotes NH or O, Y denotes Ar-diyl, T denotes piperidin-1-yl, 2-oxopiperidin-1-yl, 2-oxopyrrolidin-1-yl, pyrrolidin-1-yl, 2-oxo-1H-pyridin-1-yl, 3-oxomorpholin-4-yl, morpholin-4-yl, 4-oxo-1H-pyridin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl, 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl, or $N(R^2)_2$ and, if Y=piperidine-1,4-diyl, also $R^2$ or cycloalkyl, A denotes unbranched or branched alkyl having 1-10 C atoms, in which one or two $CH_2$ groups may be replaced by O or S atoms and/or by —CH=CH— groups and/or also 1-7 H atoms may be replaced by F, Ar denotes phenyl which is unsubstituted or mono-, di- or trisubstituted by Hal, A, $OR^2$, $SO_2A$, $SO_2NH_2$, $COOR^2$ or CN, Hal denotes F, Cl, Br or I, m denotes 1 or 2, and n denotes 0, 1 or 2.

15. A compound according to claim 1, in which

D denotes phenyl which is mono substituted by Hal, $R^1$ denotes alkyl having 1, 2, 3, 4, 5 or 6 C atoms which is monosubstituted by $S(=O)(=NR^2)R^2$, $NR^2SO_2R^2$, $OSO_2R^2$, $OSO_2N(R^{2)}_2$ or $PO(OR^2)_2$, $R^2$ denotes H or alkyl having 1, 2, 3, 4, 5 or 6 C atoms, W denotes —$(CH_2)_n$—, X denotes NH or O, Y denotes phenylene which is unsubstituted or monosubstituted by A, T denotes piperidin-1-yl, 2-oxopiperidin-1-yl, 2-oxopyrrolidin-1-yl, pyrrolidin-1-yl, 2-oxo-1H-pyridin-1-yl, 3-oxomorpholin-4-yl, morpholin-4-yl, 4-oxo-1H-pyridin-1-yl, 2,6-dioxopiperidin 1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl, 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl, or $N(R^2)_2$ and, if Y=piperidine-1,4-diyl, also $R^2$ or cycloalkyl, A denotes unbranched or branched alkyl having 1-10 C atoms, in which one or two $CH_2$ groups may be replaced by O or S atoms and/or by —CH=CH— groups and/or also 1-7 H atoms may be replaced by F, Y denotes phenylene which is unsubstituted or monosubstituted by A, Hal denotes F, Cl, Br or I, m denotes 1 or 2, and n denotes 0, 1 or 2.

16. A compound, which is

2-[3-(4-chlorophenyl)ureido]—N-[4-(2-oxo-2H-pyridin-1-yl)phenyl]-4-methanesulfonylbutyramide, 2-[3-(4-chlorophenyl)ureido]—N-[4-(2-oxo-2H-pyrazin-1-yl)phenyl]-4-methanesulfonylbutyramide, 2-[3-(4-chlorophenyl)ureido]—N-[4-(3-oxomorpholin-4-yl)phenyl]-4-methanesulfonylbutyramide, (R)-2-[3(4-chlorophenyl)ureido]—N-[4-(3-oxomorpholin-4-yl)phenyl]-4-methanesulfonylbutyramide, (R)-2-[3-(4-chlorophenyl)ureido]—N-[4-(2-oxo-2H-pyridin-1-yl)phenyl]-3-methanesulfonyipropionamide, (S)-2-[3-(4-chlorophenyl)ureido]—N-[4-(2-oxo-2H-pyridin-1-yl)phenyl]-3-methanesulfonyipropionamide, (S)-2-[N-(4-chlorophenyl)carbamoyloxy]—N-[4-(3-oxomorpholin-4-yl)phenyl]-3-methanesulfonylpropionamide, (R)-2-[N-(4-chlorophenyl)carbamoyloxy]—N-[4-(3-oxomorpholin-4-yl)phenyl]-3-methanesulfonyipropionamide, (R)-2-[3-(4-chlorophenyl)ureido]—N-[4-(2-oxo-2H-pyridin-1-yl)phenyl]-4-methanesulfonylbutyramide, (S)-2-[3-(4-chlorophenyl)ureido]—N-[4-(3-oxomorpholin-4-yl)phenyl]-3-methanesulfonyipropionamide, 2-[N-4-chlorophenyl)carbamoyloxy]—N-[4-(2-oxo-2H-pyridin-1-yl)phenyl]-3-methanesulfonylpropionamide, 2-[3-(4-chlorophenyl)ureido]—N-[4-(3-oxomorpholin-4-yl)phenyl]-3-sulfopropionamide, 2-[3-(4-chlorophenyl)ureido]—N-[4-(2-oxo-2H-pyridin-1-yl)phenyl]-3-sulfopropionamide, (S)-2-[3-(4-chlorophenyl)ureido]—N-[4-(3-oxomorpholin-4-yl)phenyl]-3-(dimethoxyphosphoryl)propionamide, 2-[3(4-chlorophenyl)ureido]—N-[4-(2-oxomorpholin-1-yl)phenyl]-3-(dimethoxyphosphoryl)propionamide, 2-[3-(4-chlorophenyl)ureido]—N-[4-(3-oxopiperidin-4-yl)phenyl]-3-phosphonopropionamide, 2-[3-(4-chlorophenyl)ureido]—N-[4-(2-oxopiperidin-4-yl)phenyl]-3-(methanesulfoximinyl)butyramide, 2-[3-(4-chlorophenyl)ureido]—N-[4-(2-oxo-2H-pyridin-1-yl)phenyl]3-sulfamoylpropionamide, 2-[3-(4-chlorophenyl)ureido]—N-[4-(3-oxomorpholin-4-yl)phenyl]-3-methanesulfonylaminopropionamide, 2-[3-(4-chlorophenyl)ureido]—N-[4-(3-oxomorpholin-4-yl)phenyl]-3-sulfamoyloxypropionamide, (R)-2-[3-(4-chlorophenyl)ureido]—N-[3-methyl-4-(3-oxomorpholin-4-yl)phenyl]-3-methanesulfonyipropionamide, (R)-2-[3-(4-chlorophenyl)ureido]—N-[2-oxo-1,3-oxazinan-3-yl)phenyl-]3-methanesulfonylpropionamide, (R)-2-[3-(4-chlorophenyl)ureido]—N-[3-methyl-4-(3-oxomorpholin-4-yl)phenyl]-4-methanesulfonylbutyramide, (R)-2-[3-(4-chlorophenyl)ureido]—N-[4-(3-oxomorpholin-4-yl)phenyl]-3-sulfamoyloxypropionamide, (R)-2-[3-(4-chlorophenyl)ureidp]—N-[4-(3-oxomorpholin-4-yl)phenyl]-3(dimethoxyphosphoryl)propionamide, (R)-2-[3-(4-chlorophenyl)ureido]—N-[3-methyl-4-(3-oxomorpholin-4-yl)phenyl]-3-(dimethoxyphosphoryl)propionamide, or (S)-2-[3-(4-chlorophenyl)ureido]—N-[3-methyl-4-(3-oxomorpholin-4-yl)phenyl]-3-(dimethoxyphosphoryl)propionamide.

17. A process for preparing a compound of formula I according to claim 1, comprising
a) reacting a compound of formula II

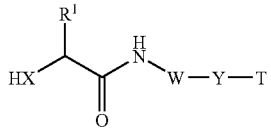

in which
R$^1$, T, W, X and Y have the meaning indicated for the compound of formula I, with a compound of formula III

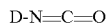

in which
D has the meaning indicated for the compound of formula I,
or
b) reacting a compound of formula IV

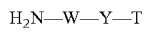

in which W, Y and T have the meaning indicated for the compound of formula I, with a compound of formula V

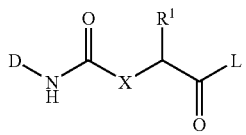

in which
L denotes Cl, Br, I or a free or reactively functionally modified OH group and R$^1$, X and D have the meanings indicated for the compound of formula I,
or
c) a radical R$^1$ is convened into another radical R$^1$ by oxidizing the radical R$^1$, and/or a base or acid of a compound of formula I is convened into one of its salts.

18. A method for inhibiting coagulation factor Xa, comprising administering an effective amount of a compound of claim 1.

19. A method for inhibiting coagulation factor VIIa, comprising administering an effective amount of a compound of claim 1.

20. A pharmaceutical composition, comprising at least one compound of formula I according to claim 1 and a pharmaceutically acceptable excipient and/or adjuvant.

21. A pharmaceutical composition according to claim 20, further comprising a further pharmaceutically active ingredient.

22. A method for treating thromboses, myocardial infarction, arteriosclerosis, angina pectoris, restenosis after angioplasty, claudicatio intermittens, or migraine, comprising administering to a subject in need thereof an effective amount of a pharmaceutical composition according to claim 20.

23. A set or kit comprising separate packs of
(a) a compound of formula I according to claim 1, and
(b) a further pharmaceutically active ingredient.

24. A method according to claim 22, further comprising administering a further pharmaceutically active ingredient.

25. A compound of formula I

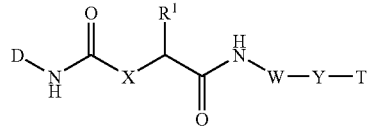

in which
D denotes phenyl or pyridyl, each of which is unsubstituted or mono- or polysubstituted by Hal, A, OR$^2$, N(R$^2$)$_2$, NO$_2$, CN, COOR$^2$ or CON(R$^2$)$_2$,
R$^1$ denotes A, which is mono-, di- or trisubstituted by SO$_2$N(R$^{2'}$)$_2$, SO$_3$R$^{2'}$, S(=O)(=NR$^{2'}$)R$^2$, NR$^2$SO$_2$R$^2$, OSO$_2$R$^2$,OSO$_2$N(R$^2$)$_2$ or PO(OR$^2$)$_2$ and may additionally be mono- or disubstituted by OR$^3$, N(R$^3$)$_2$, CN, COOR$^3$ or CON(R$^3$)$_2$, and may additionally be mono-, di- or trisubstituted by S(O)$_m$R$^2$, SO$_2$N(R$^2$)$_2$ or SO$_3$R$^2$,
R$^2$ denotes H, A, —[C(R$^3$)$_2$]$_n$—Ar', —[C(R$^3$)$_2$]$_n$-Het', —[C(R$^3$)$_2$]$_n$-cycloalkyl, —[C(R$^3$)$_2$]$_n$—N(R$^3$)$_2$ or —[C(R$^3$)$_{2]n}$-OR$^3$,
R$^{2'}$ denotes —[C(R$^3$)$_2$]$_n$-Ar', —[C(R$^3$)$_2$]$_n$-Het', —[C(R$^3$)$_2$]$_n$-cycloalkyl, —[C(R$^3$)$_2$]$_n$—N(R$^3$)$_2$ or —[C(R$^3$)$_{2]n}$ OR$^3$,
R$^3$ denotes H or A,
W denotes —[C(R$^3$)$_2$]$_n$—,
X denotes NR$^3$ or O,
Y denotes alkylene, cycloalkylene, Het-diyl or Ar-diyl,
T denotes a mono- or bicyclic saturated, unsaturated or aromatic carbo- or heterocycle having 0 to 4 N, O and/or S atoms, which may be mono-, di- or trisubstituted by =O, R$^2$, Hal, A, —[C(R$^3$)$_2$]$_n$-AR,—[C(R$^3$)$_2$]$_n$ -Het, —[C(R$^3$)$_2$]$_n$-cycloalkyl, OR$^2$, N(R$^2$)$_2$, NO$_2$,CN, COOR$^2$, CON(R$^2$)$_2$, NR$^2$COA, NR$^2$CON(R$^2$)$_2$, NR$^2$SO$_2$A, COR$^2$, SO$_2$NR$^w$ and/or S(O)$_n$A,
or N(R$^2$)$_2$
and, if Y=piperidine-1,4-diyl, also R$^2$ or cycloalkyl,
A denotes unbranched or branched alkyl having 1-10 C atoms, in which one or two CH$_2$ groups may be replaced by O or S atoms and/or by —CH=CH— groups and/or also 1-7 H atoms may be replaced by F,
Ar denotes phenyl, naphthyl or biphenyl, each of which is unsubstituted or mono-, di- or trisubstituted by Hal, A, OR$^2$, N(R$^2$)$_2$, NO$_2$, CN, COOR$^2$, CON(R$^2$)$_2$, NR$^2$COA, NR$^2$SO$_2$A, COR$^2$, SO$_2$N(R$^2$)$_2$—[C(R$^3$)$_2$]$_n$—COOR$^2$, —O—[C(R$^3$)$_2$]$_o$—COOR$^2$, SO$_3$H or S(O)$_n$A,
Ar' denotes phenyl which is unsubstituted or mono-, di- or trisubstituted by Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$N(R$^3$)$_2$, S(O)$_n$A, —[C(R$^3$)$_2$]$_n$ COOR$^3$ or —O—[C(R$^3$)$_2$]$_o$—COOR$^3$,
Het denotes a mono- or bicyclic saturated, unsaturated or aromatic heterocycle having 1 to 4 N, O and/or S atoms, which may be unsubstituted or mono-, di- or trisubstituted by carbonyl oxygen (=O), =S, =N(R$^2$)$_2$, Hal, A, —[C(R$^3$)$_2$]$_n$-Het', —[C(R$^3$$_2$]$_n$-cycloalkyl, —[C(R$^3$)$_2$]$_n$-OR$^2$, —[C(R$^3$)$_2$]$_n$N(R$^3$)$_2$, NO$^2$, CN, —[C(R$^3$)$_2$]$_n$—COOR$^2$, —[C(R$^3$)$_2$]$_n$-CON(R$^2$)$_2$, —[C(R$^3$)$_2$]$_n$-NR$^2$COA, NR$^2$CON(R$^2$)$_2$, —[C(R$^3$)$_2$]$_n$-NR$^2$SO$_2$A, COR$^2$, SO$_2$N(R$^2$)$_2$ and/or S(O)$_n$A,
Het'denotes a mono- or bicyclic saturated, unsaturated or aromatic heterocycle having 1 to 4 N, O and/or S atoms, which may be unsubstituted or mono- or disubstituted by carbonyl oxygen, (=)), =S, =N(R$^3$)$_2$, Hal, A, OR$^3$, $N(R^3)_2$, CN, $COOR^3$, $CON(R^3)_2$, $NR^3COA$, $NR^3CON(R^3)_2$, $NR^3SO_2A$, $COR^3$, $SO_2N(R^3)_2$ and/or $S(O)_nA$, Hal denotes F, Cl, Br or I, m denotes 1 or 2, n denotes 0, 1 or 2, and o denotes 1, 2 or 3, or a pharmaceutically acceptable salt thereof

26. A compound according to claim 1, in which $R^1$ denotes A, which is mono-, di- or trisubstituted by $NR^2SO_2R^2$, $OSO_2R^2$, $OSO^2N(R^2)_2$ or $PO(OR^2)_2$, and may additionally be mono- or disubstituted by $OR^3$, $N(R^3)_2$, CN, $COOR^3$ or $CON(R^3)_2$, and may additionally be mono-, di- or trisubstituted by $S(O)_mR^2$, $SO_2N(R^2)_2$, $SO_3R^2$, or $S(=O)(=NR^2)R^2$.

27. A compound of formula I

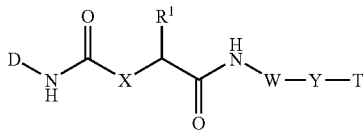

I in which

D denotes phenyl or pyridyl, each of which is unsubstituted or mono- or polysubstituted by Hal, A, $OR^2$, $N(R^2)_2$, $NO_2$, CN, $COOR^2$ or $CON(R^2)_2$, $R^1$ denotes A, which is mono-, di- or trisubstituted by $S(O)_mR^2$, $SO_2N(R^2)_2$, $SO_3R^2$, $S(=O)(=NR^2)R^2$, $NR^2SO_2R^2$, $OSO_2N(R^2)$, $OSO_2N(R^2)_2$ or $PO(OR^2)_2$ and may additionally be mono- or disubstituted by $OR^3$, $N(R^3)_2$, CN, $COOR^3$ or $CON(R^3)_2$, $R^2$ denotes H, A, —$[C(R^3)2]_n$—Ar', —$[C(R^3)_2]_n$-Het', —$[C(R^3)_2]_n$-cycloalkyl, —$[CR^3)_2]_n$—$N(R^3)_2$ or —$[C(R^3)_2]_n$-$OR^3$, $R^3$ denotes H or A, W denotes —$[C(R^3)_2]_n$, X denotes $NR^3$ or O, Y denotes alkylene, cycloalkylene, Het-diyl or Ar-diyl, T denotes a mono- or bicyclic saturated, unsaturated or aromatic carbo- or heterocycle having 0 to 4 N, O and/or S atoms, which is mono-, di- or trisubstituted by =O, and which in addition may be mono-, di- or trisubstituted by $R^2$, Hal, A, —$[C(R^3)_2]_n$—Ar, —$[C(R^3)_2]_n$-Het, —$[C(R^3)_2]_n$-cycloalkyl, $OR^2$, $N(R^2)_2$, $NO_2$, CN, $COOR^2$, $CON(^2)_2$, $NR^2COA$, $NR^2CON(R^2)_2$, $NR^2SO_2A$, $COR^2$, $SO_2NR^2$ and/or $S(O)_nA$, or $N(R^2)_2$ and, if Y=piperidine-1,4-diyl, also $R^2$ or cycloalkyl, A denotes unbranched or branched alkyl having 1-10 C atoms, in which one or two $CH_2$ groups may be replaced by O or S atoms and/or by —CH=CH— groups and/or also 1-7 H atoms may be replaced by F, Ar denotes phenyl, naphthyl or biphenyl, each of which is unsubstituted or mono-, di- or trisubstituted by Hal, A, $OR^2$, $N(R^2)_2$, $NO_2$, CN, $COOR^2$, $CON(R^2)_2$ $NR^2COA$, $NR^2SO^2A$, $COR^2$, $SO_2N(R^2)_2$, —$[C(R^3)_2]_n$—$COOR^2$, —O—$[C(R^3)_2]_o$—$COOR^2$, $SO^2H$ or $S(O)_nA$, Ar' denotes phenyl which is unsubstituted or mono-, di- or trisubstituted by Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$, $S(O)_nA$, —$[C(R^3)_2]_n$-$COOR^3$ or —O—$[C(R^3)_2]_o$—$COOR^3$, Het denotes a mono- or bicyclic saturated, unsaturated or aromatic heterocycle having 1 to 4 N, O and/or S atoms, which may be unsubstituted or mono-, di- or trisubstituted by carbonyl oxygen (=O), =S, =$N(R^2)_2$, Hal, A, —$[C(R^3)_2]_n$—Ar, —$[C(R^3)_2]_n$-Het', —$[C(R^3)_2]_n$-cycloalkyl, —$[C(R^3)_2]_n$-$OR^2$, —$[C(R^3)_2]_n$—$N(R^2)_2$, $NO_2$, CN, —$[C(R^3)_2]_n$—$COOR^2$, —$[C(R^3)_2]_n$-$CON(R^2)_2$—$[C(R^3)_2]_n$-$NR^2COA$, $NR^2CON(R^2)_2$, —$[C(R^3)_2]_n$-$NR^2SO^2A$, $COR^2$, $SO_2N(R^2_2$ and/or $S(O)_nA$, Het' denotes a mono- or bicyclic saturated, unsaturated or aromatic heterocycle having 1 to 4 N, O and/or S atoms, which may be unsubstituted or mono- or disubstituted by carbonyl oxygen, =S, =$N(R^3)_2$, Hal, A, $OR^3$, $N(R^3)_2$, CN, $COOR^3$, $CON(R^3)_2$, $NR^3COA$, $NR^3CON(R^3)_2$, $NR^3SO_2A$, $COR^3$, $SO_2N(R^3)_2$ and/or $S(O)_nA$, Hal denotes F, Cl, Br or I, m denotes 1 or 2, n denotes 0, 1 or 2, and o denotes 1, 2 or 3, or a pharmaceutically acceptable salt thereof

28. A compound according to claim 27, in which

D denotes phenyl which is monosubstituted by Hal, $R^1$ denotes alkyl having 1, 2, 3, 4, 5 or 6 C atoms which is monosubstituted by $S(O)_mR^2$, $SO_2N(R^2)_2$, $SO_3R^2$, $S(=O)(=NR^2)R^2$, $NR^2SO^2R^2$, $OSO_2R^2$, $OSO_2N(R^2)_2$ or $PO(OR^2)_2$, $R^2$ denotes H or alkyl having 1, 2, 3, 4, 5 or 6 C atoms, W denotes —$(CH_2)_n$—, X denotes NH or O, Y denotes Ar-diyl, T denotes a mono- or bicyclic saturated, unsaturated or aromatic heterocycle having 1 to 2 N and/or O atoms which is mono- or disubstituted by =O, or $N(R^2)_2$ and, if Y=piperidine-1,4-diyl, also $R^2$ or cycloalkyl, A denotes unbranched or branched alkyl having 1-10 C atoms, in which one or two $CH_2$ groups may be replaced by O or S atoms and/or by —CH=CH— groups and/or also 1-7 H atoms may be replaced by F, Ar denotes phenyl which is unsubstituted or mono-, di- or trisubstituted by Hal, A, $OR^2$, $SO_2A$, $SO_2NH_2$, $COOR^2$ or CN, Hal denotes F, Cl, Br or I, m denotes 1 or 2, and n denotes 0, 1 or 2.

29. A compound according to claim 1, in which

T denotes a mono- or bicyclic saturated, unsaturated or aromatic carbo- or heterocycle having 0 to 4 N, O and/or S atoms, which is mono-, di- or trisubstituted by =O, and which in addition may be mono-, di- or trisubstituted by $R^2$, Hal, A, —$[C(R^3)_2]_n$-AR, —$[C(R^3)_2]_n$-Het, —$[C(R^3)_2]_n$- cycloalkyl, $OR^2$, $N(R^2)_2$, $NO_2$, CN, $COOR^2$, $CON(R^2)_2$, $NR^2COA$, $NR^2CON(R^2)_2$, $NR^2SO_2$ and/or $S(O)_nA$.

30. A compound according to claim 25, in which

T denotes a mono- or bicyclic saturated, unsaturated or aromatic carbo- or heterocycle having 0 to 4 N, O and/or S atoms, which is mono-, di- or trisubstituted by =O, and which in addition may be mono-, di- or trisubstituted by R2, Hal, A,—$[C(R^3)_2]_n$—Ar, —$[C(R^3)_2]_n$-Het, —$[C(R^3)_2]_n$-cycloalkyl, $OR^2$, $N(R^2)_2$, $NO_2$, CN, $COOR^2$, $CON(R^2)_2$, $NR^2COA$, $NR^2CON(R^2)_2$, $NR^2SO_2A$, $COR^2$, $SO_2NR^2$ and/or $S(O)_nA$.

31. A compound according to claim 27, in which

T denotes a mono- or bicyclic saturated, unsaturated or aromatic carbo- or heterocycle having 0 to 4 N, O and/or S atoms, which is mono-, di- or trisubstituted by =O, and which in addition may be mono-, di- or trisubstituted by R2, Hal, A,—$[C(R^3)_2]_n$—Ar, —$[C(R^3)_2]_n$-Het, —$[C(R^3)_2]_n$-cycloalkyl, $OR^2$, $N(R^2)_2$, $NO_2$, CN, $COOR^2$, $CON(R^2)_2$, $NR^2COA$, $NR^2CON(R^2)_2$, $NR^2SO_2A$, $COR^2$, $SO_2NR^2$ and/or $S(O)_nA$.

32. A compound according to claim 27, in which T denotes or $N(R^2)_2$.

33. A compound according to claim 27, in which T denotes $R^2$ or cycloalkyl, and Y is piperidine-1,4-diyl.

* * * * *

UNITED STATES PATENT AND TRADEMARK OFFICE
CERTIFICATE OF CORRECTION

PATENT NO. : 7,598,241 B2  Page 1 of 1
APPLICATION NO. : 10/543109
DATED : October 6, 2009
INVENTOR(S) : Dorsch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1023 days.

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,598,241 B2
APPLICATION NO. : 10/543109
DATED : October 6, 2009
INVENTOR(S) : Dieter Dorsch Page 1 of 2

It is certified that error appears in the above-identified patent and that said Letters Patent is hereby corrected as shown below:

Column 30, line 29 reads: "$R^{2, oso}{}_2R^2$, $OSO_2N(R^2)_2$ or $PO(OR^2)_2$."
Should read: --$R^{2,} OSO_2R^2$, $OSO_2N(R^2)_2$ or $PO(OR^2)_2$.--

Column 32, line 23 reads: "lin-4-yl)phenyl]-3-methanesulfonyiporpionamide,"
Should read: --lin-4-yl)phenyl]-3-methanesulfonylporpionamide,--

Column 32, line 34 reads: "2-[3-(4-chlorophenyl)ureido]-N-[4-(2-oxomorpholin-1-"
Should read: --2-[3-(4-chlorophenyl)ureido]-N-[4-(2-oxopiperidin-1- --

Column 32, line 36 reads: "2-[3-(4-chlorophenyl)ureido]-N-[4-(3- oxopiperidin-4-"
Should read: --2-[3-(4-chlorophenyl)ureido]-N-[4-(3-oxomorpholin-4- --

Column 32, line 39 reads: "2-[3-(4-chlorophenyl)ureido]-N-[4-(2-oxopiperidin-4-"
Should read: : --2-[3-(4-chlorophenyl)ureido]-N-[4-(3-oxomorpholin-4- --

Column 32, line 40 reads: "yl)phenyl[-3-(methanesulfoximinyl)butyramide,"
Should read: --(methanesulfoximinyl)butyramide,--

Column 32, line 42 reads: "1-yl)phenyl]3-sulfamoylpropionamide,"
Should read: --1-yl)phenyl]-3-sulfamoylpropionamide,--

Column 33, line 42 reads: "c) a radical $R^1$ is convened into another radical $R^1$ by"
Should read: --c) radical $R^1$ is converted into another radical $R^1$ by--

Column 33, line 44 reads: "compound of formula I is convened into one of its salts"
Should read: --compound of formula I is converted into one of its salts--

Column 34, line 54 reads: "$COOR^3$ or $-0-[C(R^3)_2]_o-COOR^3$,"
Should read: -- - $COOR^3$ or $-0-[C(R^3)_2]_o-COOR^3$,--

Signed and Sealed this

Seventh Day of December, 2010

David J. Kappos
*Director of the United States Patent and Trademark Office*

CERTIFICATE OF CORRECTION (continued)
U.S. Pat. No. 7,598,241 B2

Column 34, line 59 reads: "-[C($R^3$)$_2$]$_n$- Het', -[C($R^3$)$_2$]$_n$-cycloalkyl, -[C($R^3$)$_2$]$_n$-"
Should read: -- -[C($R^3$)$_2$]$_n$-Ar, -[C($R^3$)$_2$]$_n$-Het', -[C($R^3$)$_2$]$_n$-cycloalkyl, -[C($R^3$)$_2$]$_n$- --

Column 34, line 64 reads: "Het'denotes a mono- or bicyclic saturated, unsaturated or"
Should read: --Het' denotes a mono- or bicyclic saturated, unsaturated or--

Column 34, line 67 reads: "by carbonyl oxygen,((=)), =S, =N($R^3$)$_2$, Hal, A, O$R^3$,"
Should read: --by carbonyl oxygen, =S, =N($R^3$)$_2$, Hal, A, O$R^3$,--

Column 35, line 36 reads: "-[C($R^3$)$_2$]$_n$-cycloalkyl, -[C$R^3$)$_2$]$_n$-N($R^3$)$_2$ or -[C"
Should read: -- -[C($R^3$)$_2$]$_n$-cycloalkyl, -[C($R^3$)$_2$]$_n$-N($R^3$)$_2$ or -[C--

Column 35, line 39 reads: "W denotes -[C($R^3$)$_2$]$_n$,"
Should read: --W denotes -[C($R^3$)$_2$]$_n$-,--

Column 35, line 47 reads: "($R^3$)$_2$]$_{n\text{-Het}}$, -[C(R3)2]n-cycloalkyl, O$R^2$, N($R^2$)$_2$, NO$_2$,"
Should read: --($R^3$)$_2$]$_n$-Ar, -[C($R^3$)$_2$]$_n$-Het, -[C($R^3$)$_2$]$_n$-cycloalkyl, O$R^2$, N($R^2$)$_2$, NO$_2$,--

Column 35, line 59 reads: "-O-[C($R^3$)$_2$]$_o$-COO$R^2$, SO$^2$H or S(O)$_n$A,"
Should read: -- -O-[C($R^3$)$_2$]$_o$-COO$R^2$, SO$_3$H or S(O)$_n$A,--

Column 36, line 6 reads: "N$R^2$SO$^2$A, CO$R^2$, SO$_2$N($R^2$$_2$ and/or S(O)$_n$A,"
Should read: --N$R^2$SO$_2$A, CO$R^2$, SO$_2$N($R^2$)$_2$ and/or S(O)$_n$A,--

Column 36, line 11 reads: "$_2$, CN, COO$R^3$, CON($R^3$)$_2$, N$R^3$COA, N$R^3$CON($R^3$)$_2$,"
Should read: --$_2$, NO$_2$, CN, COO$R^3$, CON($R^3$)$_2$, N$R^3$COA, N$R^3$CON($R^3$)$_2$,--

Column 36, line 50 reads: "CON($R^2$)$_2$, N$R^2$COA, N$R^2$CON($R^2$)$_2$, N$R^2$SO and/or"
Should read: --CON($R^2$)$_2$, N$R^2$COA, N$R^2$CON($R^2$)$_2$, N$R^2$SO$_2$A, CO$R^2$, SO$_2$N$R^2$ and/or--

Column 36, line 57 reads: " R2, Hal, A, -[C($R^3$)$_2$]$_n$-Ar, -[C($R^3$)$_2$]$_n$-Het,"
Should read: --$R^2$, Hal, A, -[C($R^3$)$_2$]$_n$-Ar, -[C($R^3$)$_2$]$_n$-Het,--

Column 36, line 66 reads: "by R2, Hal, A, -[C($R^3$)$_2$]$_n$-Ar, -[C($R^3$)$_2$]$_n$-Het, -[C"
Should read: --by $R^2$, Hal, A, -[C($R^3$)$_2$]$_n$-Ar, -[C($R^3$)$_2$]$_n$-Het, -[C--

UNITED STATES PATENT AND TRADEMARK OFFICE
CERTIFICATE OF CORRECTION

PATENT NO. : 7,598,241 B2  Page 1 of 1
APPLICATION NO. : 10/543109
DATED : October 6, 2009
INVENTOR(S) : Dieter Dorsch It is certified that error appears in the above-identified patent and that said Letters Patent is hereby corrected as shown below:

Column 32, line 42 reads: "1-yl)phenyl]3-sulfamoylpropionamide,"
Should read: --1-yl)phenyl]-3-sulfamoylpropionamide,--

Signed and Sealed this

Twenty-first Day of December, 2010

David J. Kappos
*Director of the United States Patent and Trademark Office*